US008571844B2

(12) United States Patent
Swanson et al.

(10) Patent No.: US 8,571,844 B2
(45) Date of Patent: Oct. 29, 2013

(54) METHOD AND SYSTEM FOR CHARACTERIZING TUMORS

(76) Inventors: Kristin R. Swanson, Seattle, WA (US); Ellsworth C. Alvord, Jr., Seattle, WA (US); Ellsworth C. Alvord, III, legal representative, Seattle, WA (US); Nancy Delaney Alvord, legal representative, Seattle, WA (US); James D. Murray, Litchfiled, CT (US); Russell Rockne, Shoreline, WA (US)

(*) Notice: Subject to any disclaimer, the term of this patent is extended or adjusted under 35 U.S.C. 154(b) by 467 days.

(21) Appl. No.: 12/709,367

(22) Filed: Feb. 19, 2010

(65) Prior Publication Data

US 2011/0208490 A1   Aug. 25, 2011

(51) Int. Cl.
G06G 7/48 (2006.01)
G06G 7/58 (2006.01)
G01N 33/48 (2006.01)
G01N 31/00 (2006.01)

(52) U.S. Cl.
USPC ............... 703/11; 703/12; 702/19; 702/22

(58) Field of Classification Search
None
See application file for complete search history.

(56) References Cited

PUBLICATIONS

Swanson et al. (Journal of the Neurological Sciences, 2003, 216, 1-10).*
Szeto et al. (Cancer Research, 2009, 69, 4502-4509).*
Harpold et al. (J Neuropathol. Exp. Neurol., 2007, 66(1), 1-9).*
Swanson et al. (British Journal of Cancer, 2007, 1-7).*
K. R. Swanson. Mathematical Modeling of the Growth and Control of Tumors, PhD Dissertation, University of Washington, 1999.
K. R. Swanson, E. C. Alvord Jr, J. D. Murray: A Quantitative Model for Differential Motility of Gliomas in Grey and White Matter. Cell Proliferation, 2000, 33: 317-329.
K. R. Swanson, E. C. Alvord Jr, J. D. Murray: Virtual Brain Tumors (Gliomas) Enhance the Reality of Medical Imaging and Highlights Inadequacies of Current Therapy. British Journal of Cancer, 86:14-18, 2002.
K. R. Swanson, E. C. Alvord Jr, J. D. Murray: Quantifying Efficacy of Chemotherapy of Brain Tumors (Gliomas) with Homogeneous and Heterogeneous Drug Delivery. Acta Biotheoretica, 50(4): 223-237, 2002.
E. Mandonnet, J-Y Delattre, M-L Tanguy, K. R. Swanson, A. F. Carpentier, H. Duffau, P. Cornu, R. Van Effenterre, E. C. Alvord, Jr., L. Capelle: Continuous growth of mean diameter in a subset of WHO grade II gliomas. Annals of Neurology, 53:524-528, 2003.
K. R. Swanson, E. C. Alvord Jr, J. D. Murray: Virtual Resection of Gliomas: Effect of Extent of Resection on Recurrence. Mathematical and Computer Modelling, 37(11):1177-1190, 2003 [Special Issue: "Modeling and Simulation of Tumor Development, Treatment, and Control"].

(Continued)

*Primary Examiner* — Larry D Riggs, II
(74) *Attorney, Agent, or Firm* — Browdy and Neimark, PLLC

(57) ABSTRACT

Embodiments of the present invention are directed to determining the spatial extent, aggressiveness, and other characteristics of various types of tumors, including glioma tumors that occur in brain tissue. Various embodiments of the present invention use parameterized computational models to characterize tumor growth and employ medical imaging technologies to generate images and other types of data from which values of parameters of the computational models are derived. Having obtained the parameters for a particular tumor, the extent of the tumor is estimated, with high accuracy, and other characteristics of the tumor are derived from the parameterized computational models.

37 Claims, 23 Drawing Sheets

(56) References Cited

PUBLICATIONS

K. R. Swanson, C. Bridge, J. D. Murray, E. C. Alvord Jr.: Virtual and Real Brain Tumors: Using Mathematical Modeling to Quantify Glioma Growth and Invasion. Journal of the Neurological Sciences, 216(1):1-10, 2003.

K. R. Swanson, E. C. Alvord Jr., J. D. Murray: Dynamics of a Model for Brain Tumors Reveals a Small Window for Therapeutic Intervention, Discrete and Continuous Dynamical Systems—Series B, 4(1):289-295, 2004.

H. Hatzikirou, A. Deutsch, C. Schaller, M. Simon, K. R. Swanson: Mathematical Modelling of Glioblastoma Tumour Development: A Review. Mathematical Models and Methods in Applied Sciences, 15(11), 1779-1794, Nov. 2005.

S. Jbabdi, E. Mandonnet, H. Duffau, L. Capelle, K. R. Swanson, M. Pelegrini-Issac, R. Guillevin, H. Benali: Diffusion Tensor Imaging Allows Anisotropic Growth Simulations of Low-Grade Gliomas. Magnetic Resonance in Medicine, 54:616-624, 2005.

H. L. P. Harpold, E. C. Alvord, Jr., K. R. Swanson: The Evolution of Mathematical Modeling of Glioma Growth and Invasion. Journal of Neuropathology and Experimental Neurology, 66(1):1-9, 2007.

K. R. Swanson: A Mathematical Analysis of Glioma Growth and Invasion In Vitro. Mathematical and Computer Modeling, 47:638-48, 2008, doi:10.1016/j.mcm.2007.02.024.

R. Rockne, E. C. Alvord, Jr, J. K. Rockhill, K. R. Swanson. Modeling Radiotherapy Effect in Glioma Patients. Journal of Mathematical Biology, 2008 doi:10.1007/s00285-008-0219-6.

K. R. Swanson, R. Rostomily, E. C. Alvord, Jr.: Predicting Survival of Patients with Glioblastoma by Combining a Mathematical Model and Pre-operative MR imaging Characteristics: A Proof of Principle. British Journal of Cancer, 98, 113-9, 2008, doi:10.1038/sj.bjc.6604125.

K. R. Swanson, H. L. P. Harpold, D. L. Peacock, R. Rockne, C. Pennington, L. Kilbride, R. Grant, J. Wardlaw, E. C. Alvord, Jr. Velocity of Radial Expansion of Contrast-Enhancing Gliomas and Effectiveness of X-Irradiation in Individual Patients: A Proof of Principle. Clinical Oncology, 20:301-8, 2008.

M. Szeto, G. Chakraborty, J. Hadley, R. Rockne, M. Muzi, E. C. Alvord Jr, K. A. Krohn, A. M. Spence, K. R. Swanson. Quantitative metrics of net proliferation and invasion link biological aggressiveness assessed by MRI with hypoxia assessed by FMISO-PET in glioblastomas. Cancer Research, 69(10):4502-9, 2009.

M. Assefa, R. Rockne, M. Szeto, K. R. Swanson, Mathematical Modeling of Glioma Proliferation and Diffusion. Ethnicity and Disease, 19(2) Supplement 3:60-1, 2009.

C.H. Wang, J. K. Rockhill, M. Mrugala, D. L Peacock, A. Lai, K. Jusenius, J. M. Wardlaw, T. Cloughesy, A. M. Spence, R. Rockne, E. C. Alvord, Jr, K. R. Swanson. Prognostic Significance of Growth Kinetics in Glioblastoma: Novel Insights from Combining Serial MR Imaging with a Bio-mathematical Model for Glioma Growth and Invasion. Cancer Research, 69:9133-9140, 2009.

\* cited by examiner

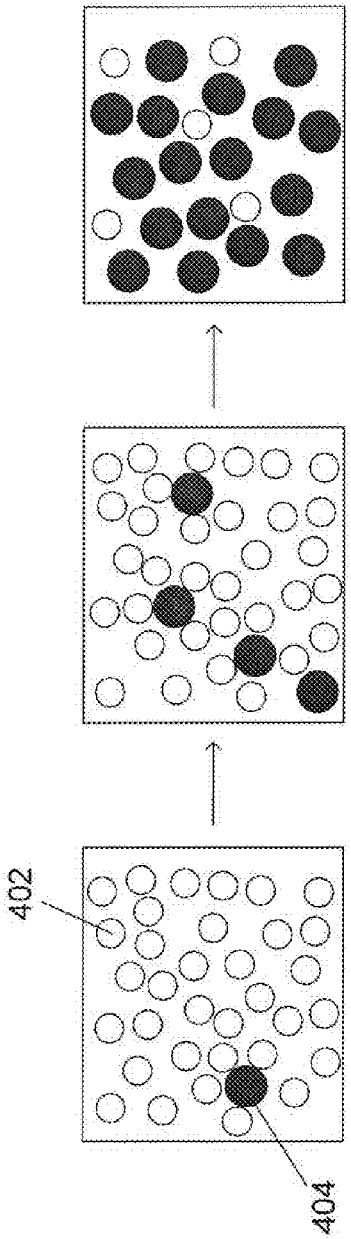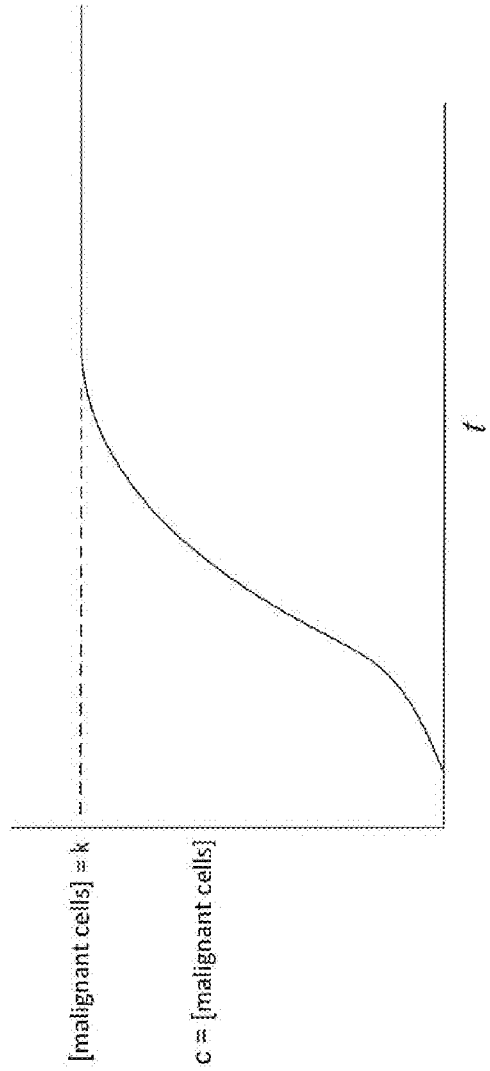

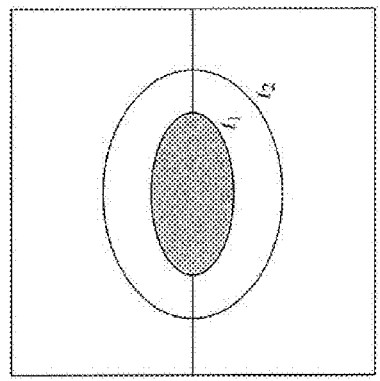
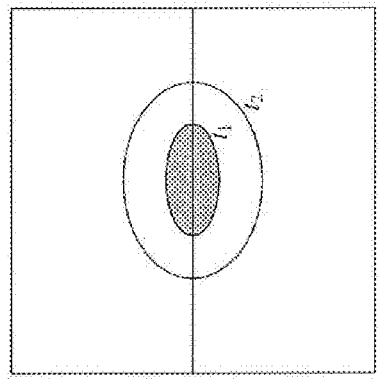
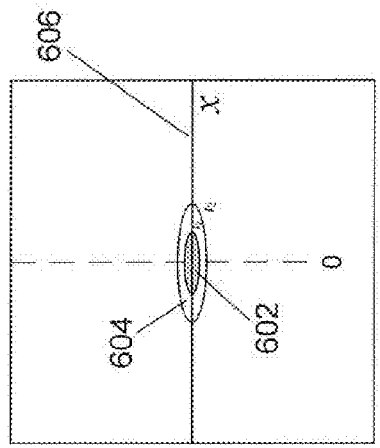
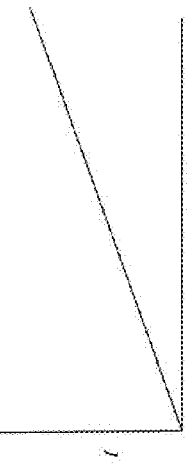
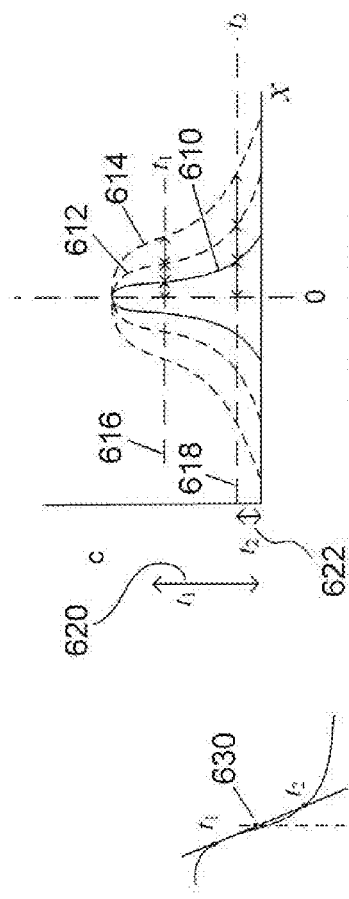
FIGURE 6A
FIGURE 6B
FIGURE 6C
FIGURE 6D
FIGURE 6E
FIGURE 6F

METHOD AND SYSTEM FOR CHARACTERIZING TUMORS

TECHNICAL FIELD

The present invention is related to characterizing tumors from data provided by various medical technologies, including imaging technologies.

BACKGROUND OF THE INVENTION

There are many different types of tumors and cancers. Gliomas are the most common type of primary brain tumors and are thought to arise from glial cells, or precursors of glial cells, that surround, support, and cooperatively interact with neurons in the brain. Because gliomas generally have already extensively invaded brain tissue before a patient is aware of the disease, gliomas are generally not curable. Glioblastomas are the most malignant and most commonly occurring type of gliomas in adults, representing about 50 percent of all gliomas. Glioblastomas are distinguished by necrosis, or tissue death, within the central portion of the tumor or irregularly spaced between vascular tissues, and by a surrounding shell of tissue diffusely invaded by peripheral tumor cells and characterized by edema. The aggressive behavior of glioblastomas is reflected in the nearly 100 percent fatality rate of patients suffering from this type of tumor within approximately two years following diagnosis, even after extensive medical intervention, including surgery, radiotherapy, and chemotherapy.

Despite continual advancements in imaging technologies, glioma cells generally invade far beyond the regions recognized as being abnormal using various types of clinical imaging technologies, including computer-aided tomography ("CT"), magnetic-resonance imaging ("MRI"), and positron emission tomography ("PET"). The extent of glioma-cell invasion is generally greater than that assumed for current radiotherapy-treatment planning. Currently, an additional shell of tissue invaded by glioma cells, having a thickness of approximately two centimeters, is assumed to surround the volume of the tumor seen in CT, MRI, or PET images. Because the extent of glioma-cell invasion is currently inaccurately modeled, therapies based on understanding the extent of glioma-cell invasion are often misapplied, leaving certain of the glioma cells that have diffused away from the tumor mass untreated or inadequately treated. The medical community continues to seek improved methodologies for characterizing both the extent of glioblastomas and other tumors as well as determining the aggressiveness of tumors and additionally characterizing the tumors in order to guide medical interventions as well as provide accurate prognoses for patients.

SUMMARY OF THE INVENTION

Embodiments of the present invention are directed to determining the spatial extent, aggressiveness, and other characteristics of various types of tumors, including glioma tumors that occur in brain tissue. Various embodiments of the present invention use parameterized computational models to characterize tumor growth and employ medical imaging technologies to generate images and other types of data from which values of parameters of the computational models are derived. Having obtained the parameters for a particular tumor, the extent of the tumor is estimated, with high accuracy, and other characteristics of the tumor are derived from the parameterized computational models.

BRIEF DESCRIPTION OF THE DRAWINGS

FIGS. 4A-D illustrate a cell-proliferation component of tumor growth.

FIGS. 6A-F illustrate tumor growth, in cross-sections through a tumor volume, as monitored by two different types of medical imaging.

values are obtained according to one embodiment of the present invention.

Figure 8:
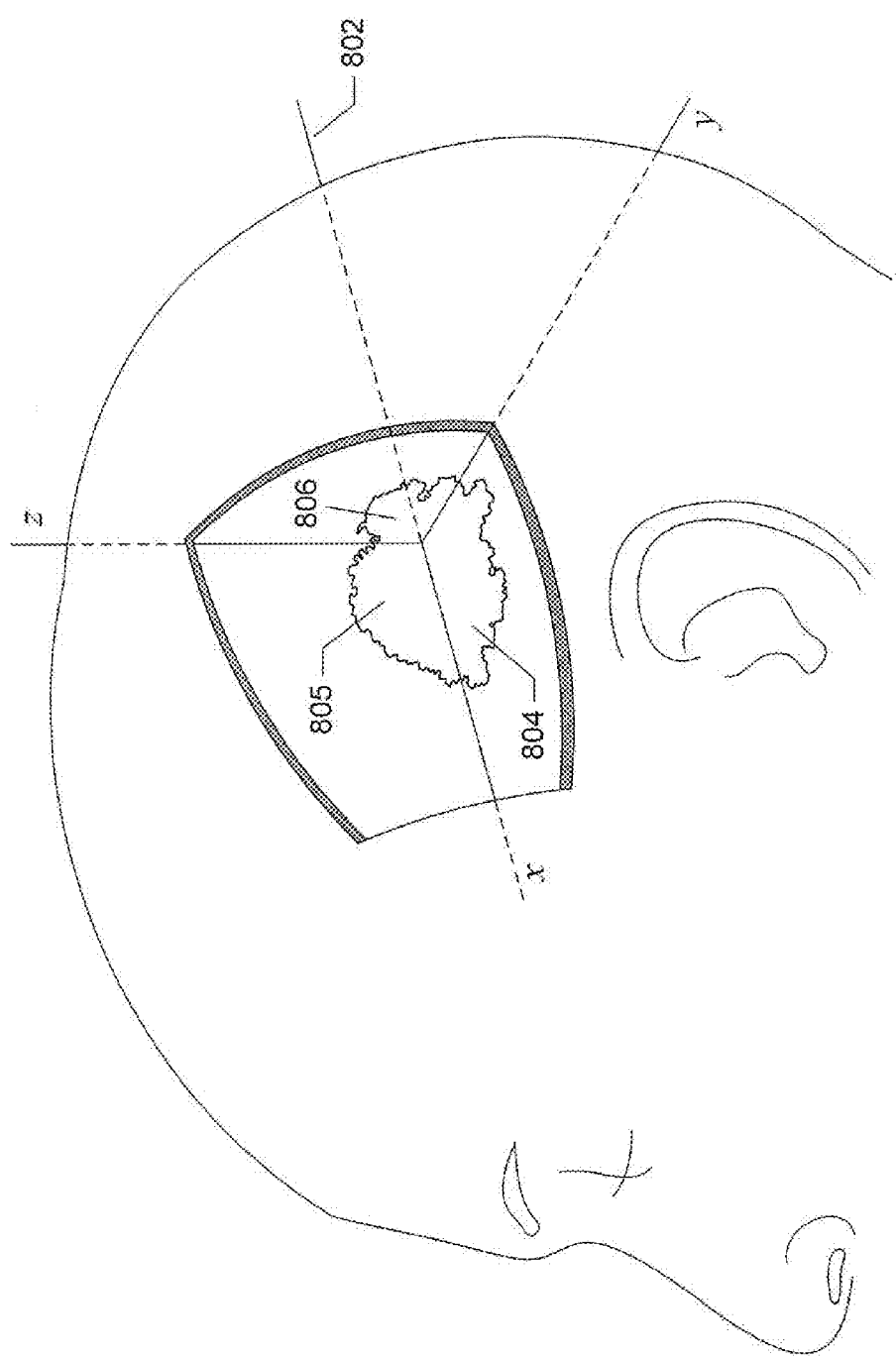

FIG. 8 illustrates determination of a scalar or tensor diffusion-coefficient field according to one embodiment of the present invention.

FIGS. 9A-E illustrate one method by which the scalar diffusion field D(r) is determined.

Figure 10:
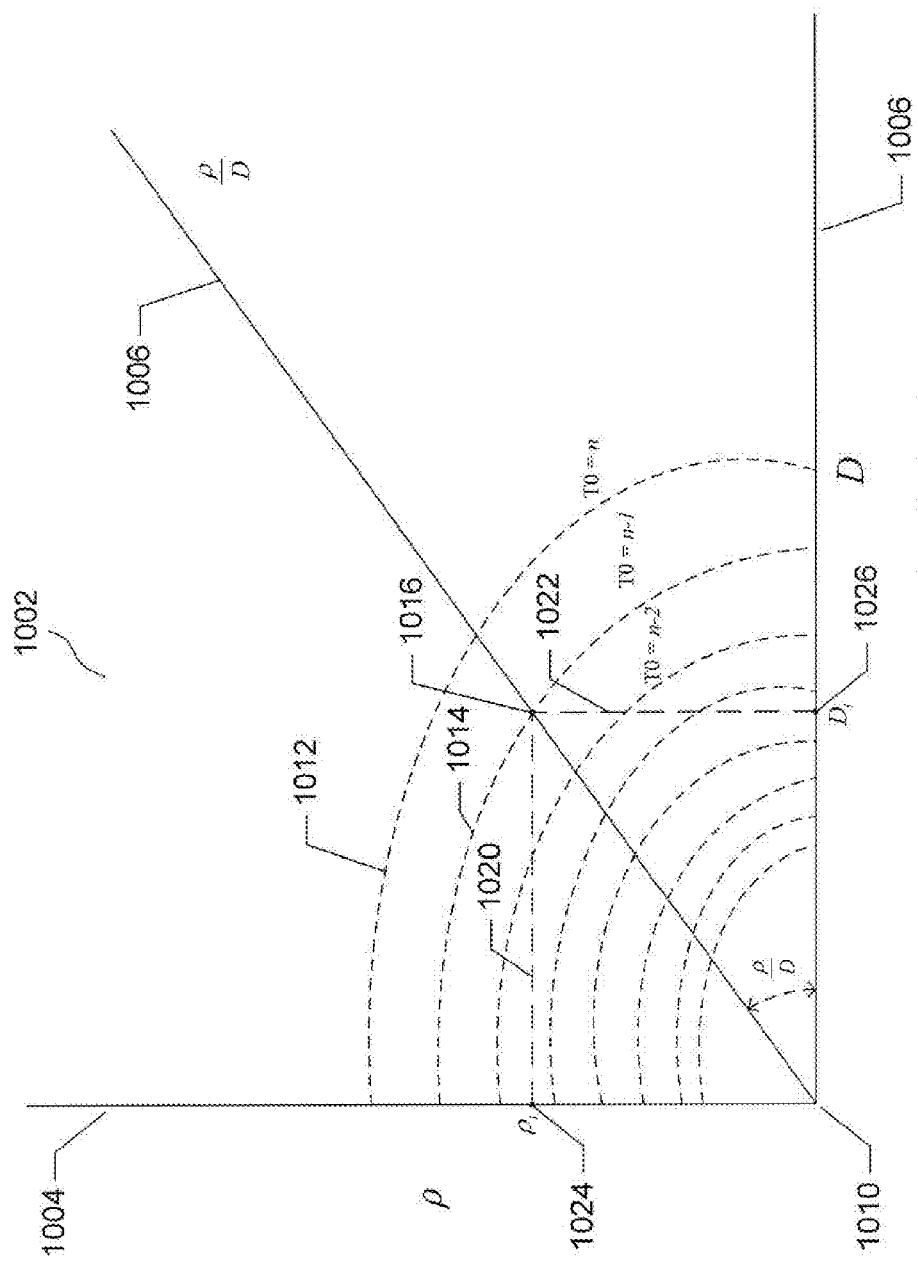

FIG. 10 illustrates an alternative method for estimating the parameters ρ and D according to one embodiment of the present invention.

Figure 11:
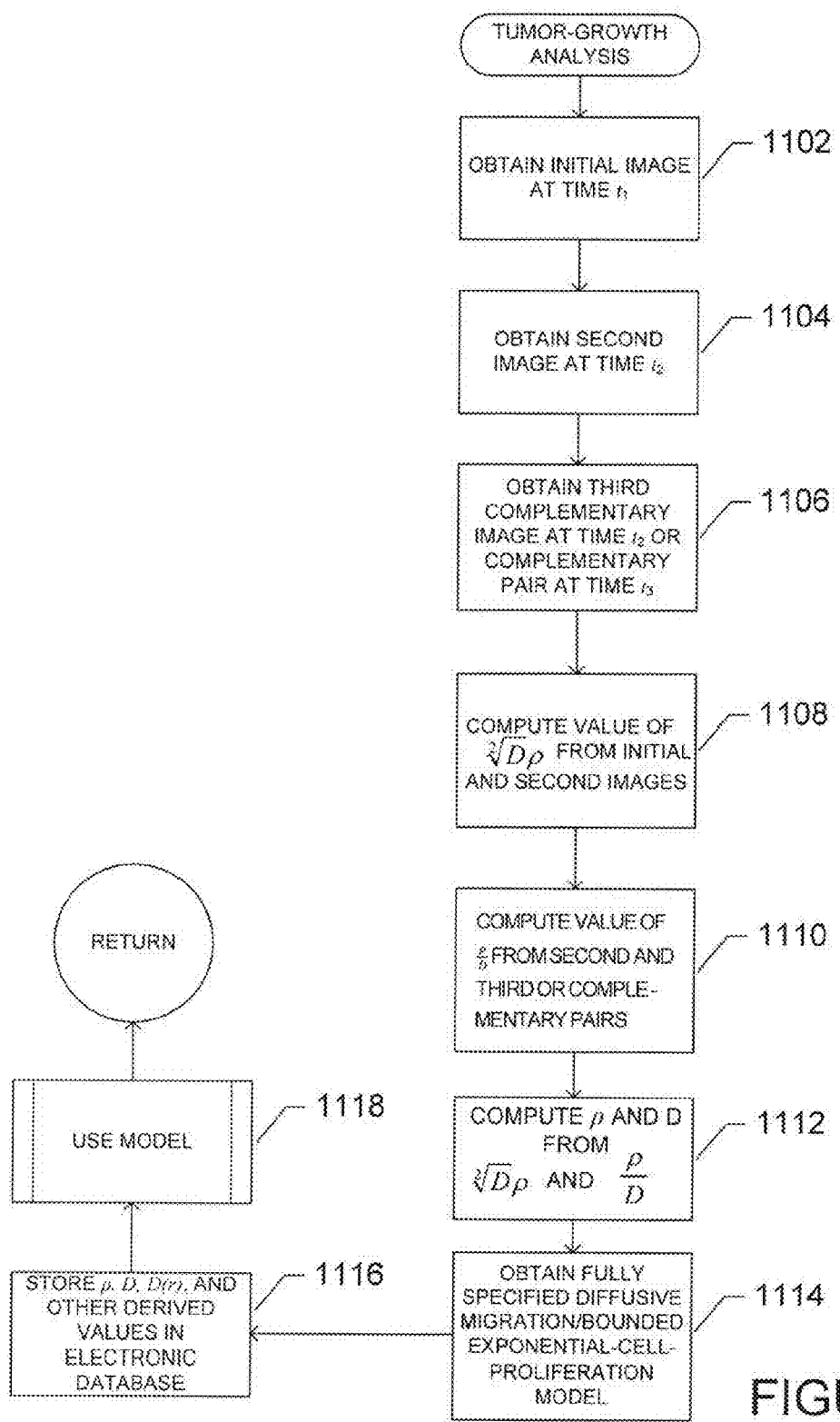

FIG. 11 provides a control-flow diagram for a routine "tumor-growth analysis" that represents one embodiment of the present invention.

Figure 12:
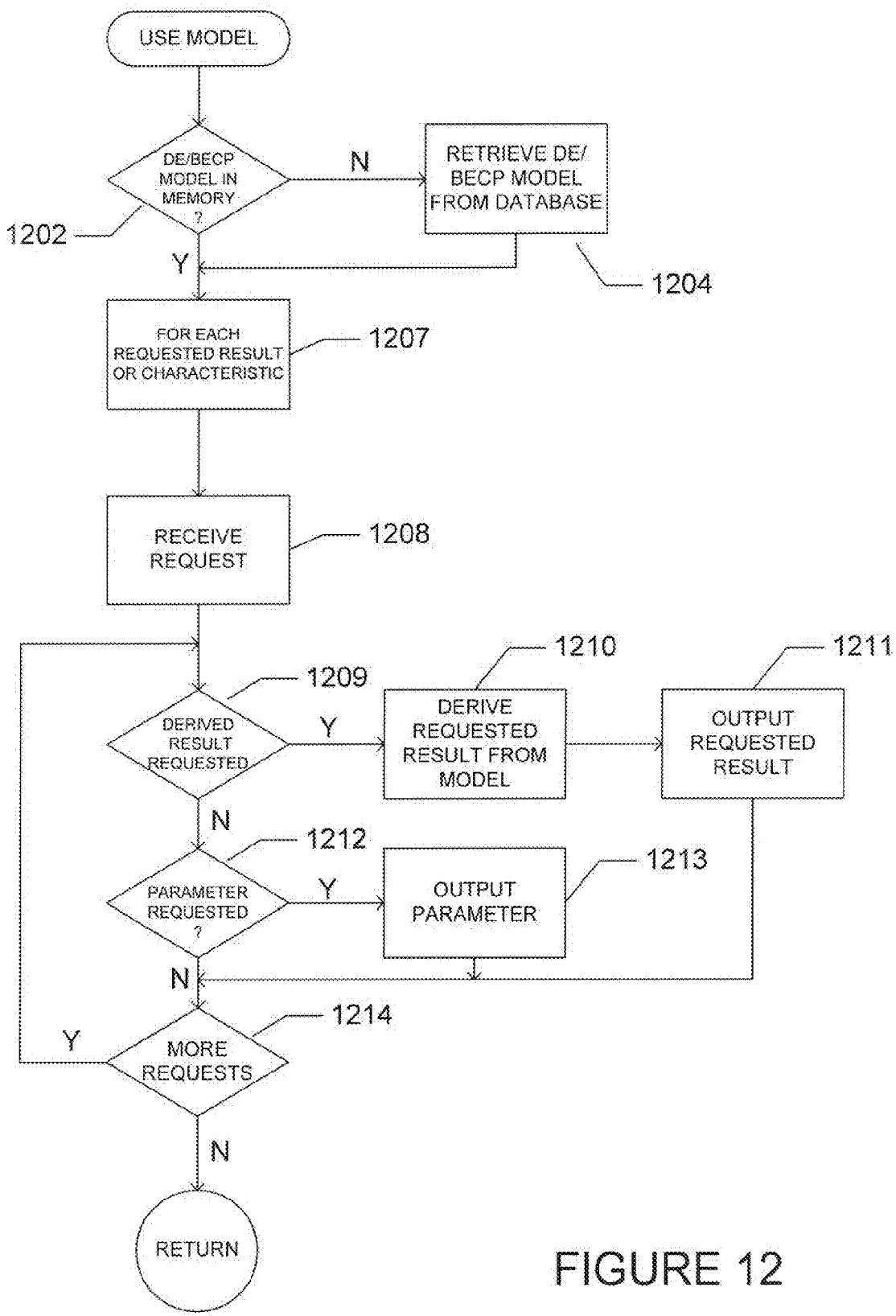

FIG. 12 provides a control-flow diagram for a routine "use model" that represents one embodiment of the present invention.

Figure 13:
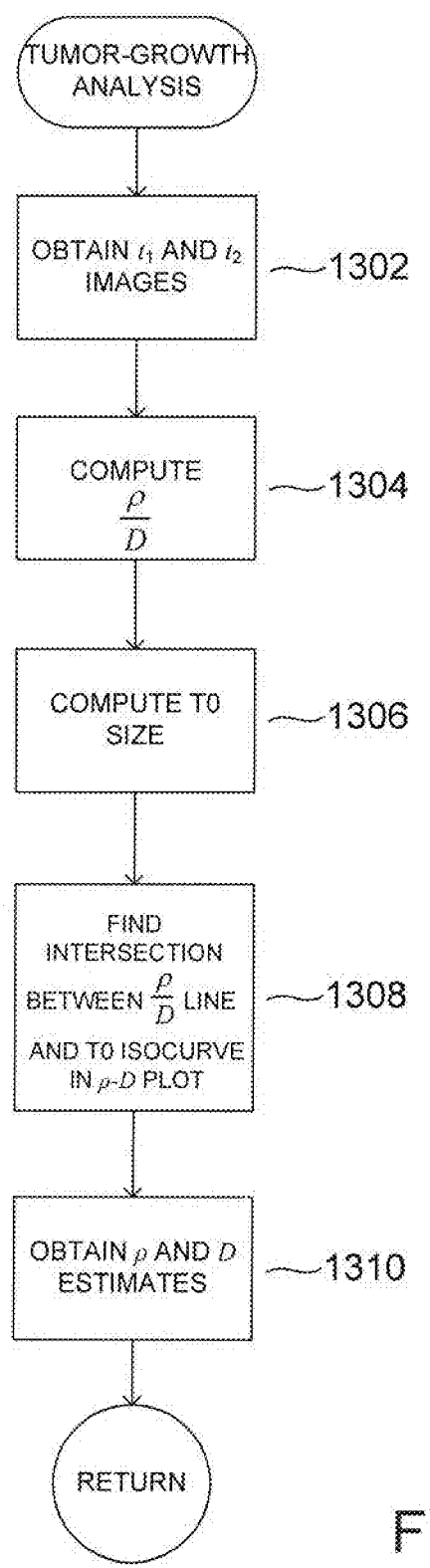

FIG. 13 provides a control-flow diagram for the alternative, single-image method for determining ρ and D parameters for a tumor.

DETAILED DESCRIPTION OF THE INVENTION

Various embodiments of the present invention are directed to computationally modeling tumor growth and then using the computational model, along with a small number of medical images of the tumor, to characterize the spatial extent of the tumor as well as other tumor parameters, including the aggressiveness of the tumor. The methods of the present invention are necessarily carried out by electronic computing systems controlled by software programs, because hand calculation would be far too slow, inaccurate, and error prone to be useful for medical diagnosis and medical therapy planning. In fact, hand calculation would be practically infeasible, due to the enormous number of calculations involved in modeling growth of a particular tumor. As with any computational-modeling undertaking, there are many different approaches to modeling tumors, with the useful approaches characterized by computational feasibility and simplicity while nonetheless providing desired levels of accuracy and reproducibility.

Figure 1A:
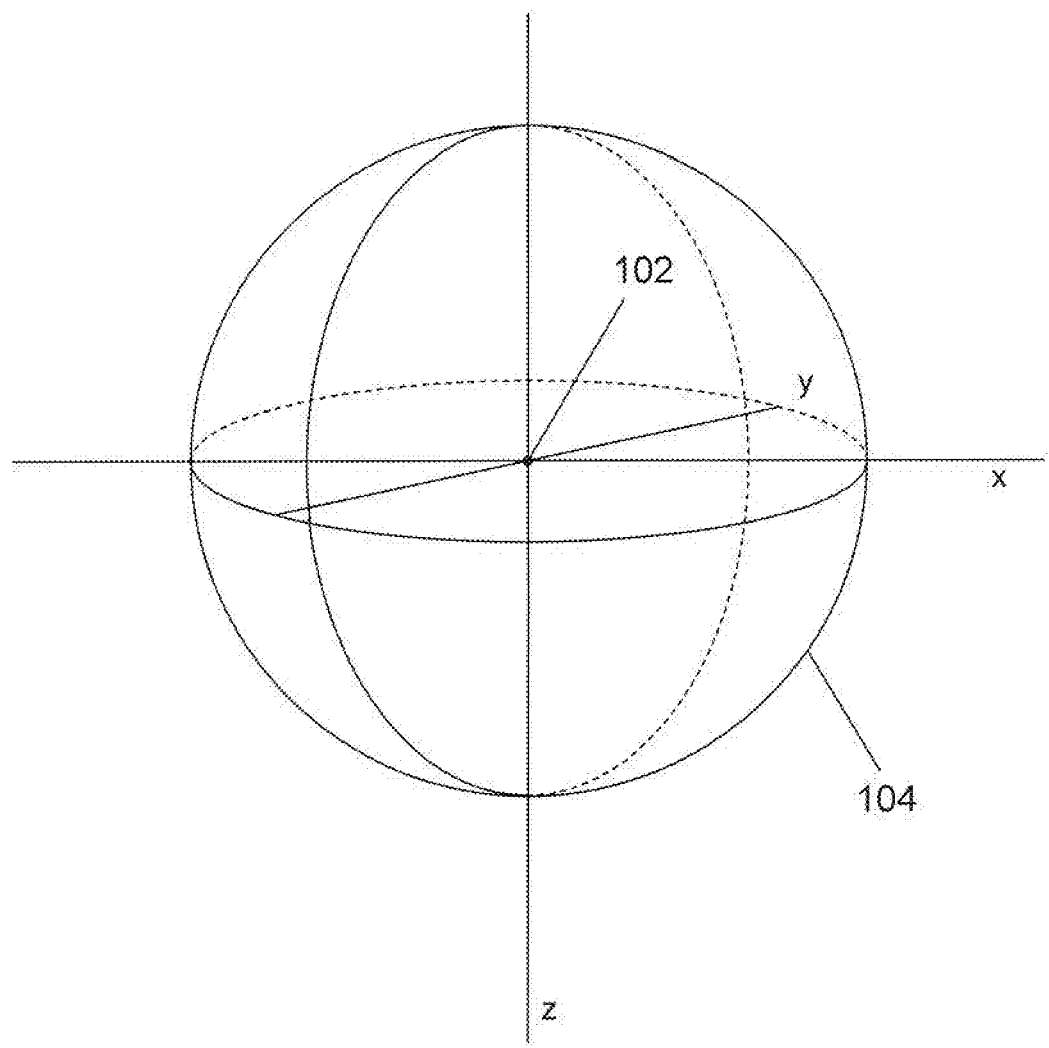
FIGS. 1A-D illustrate a simplistic computational model for tumor growth.
Figure 1B:
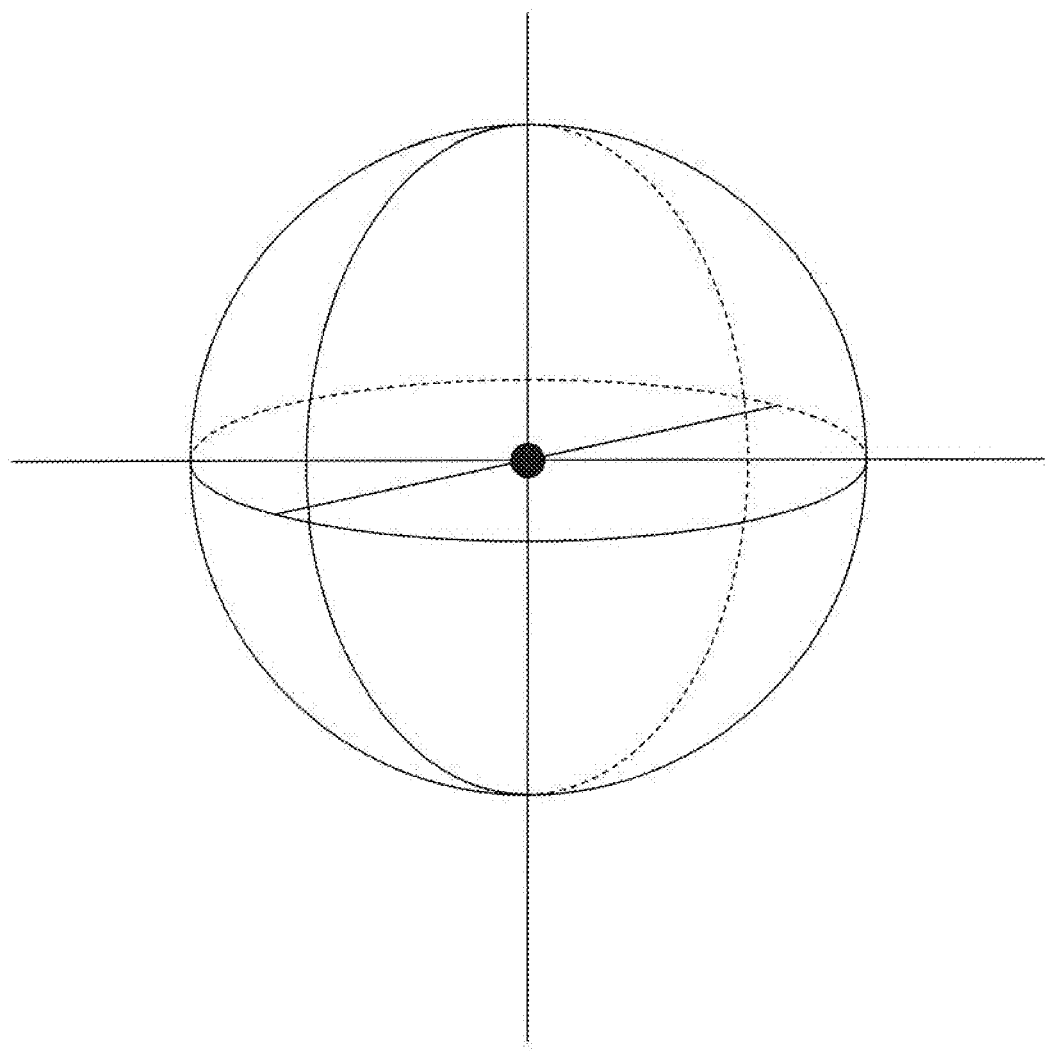
Figure 1C:
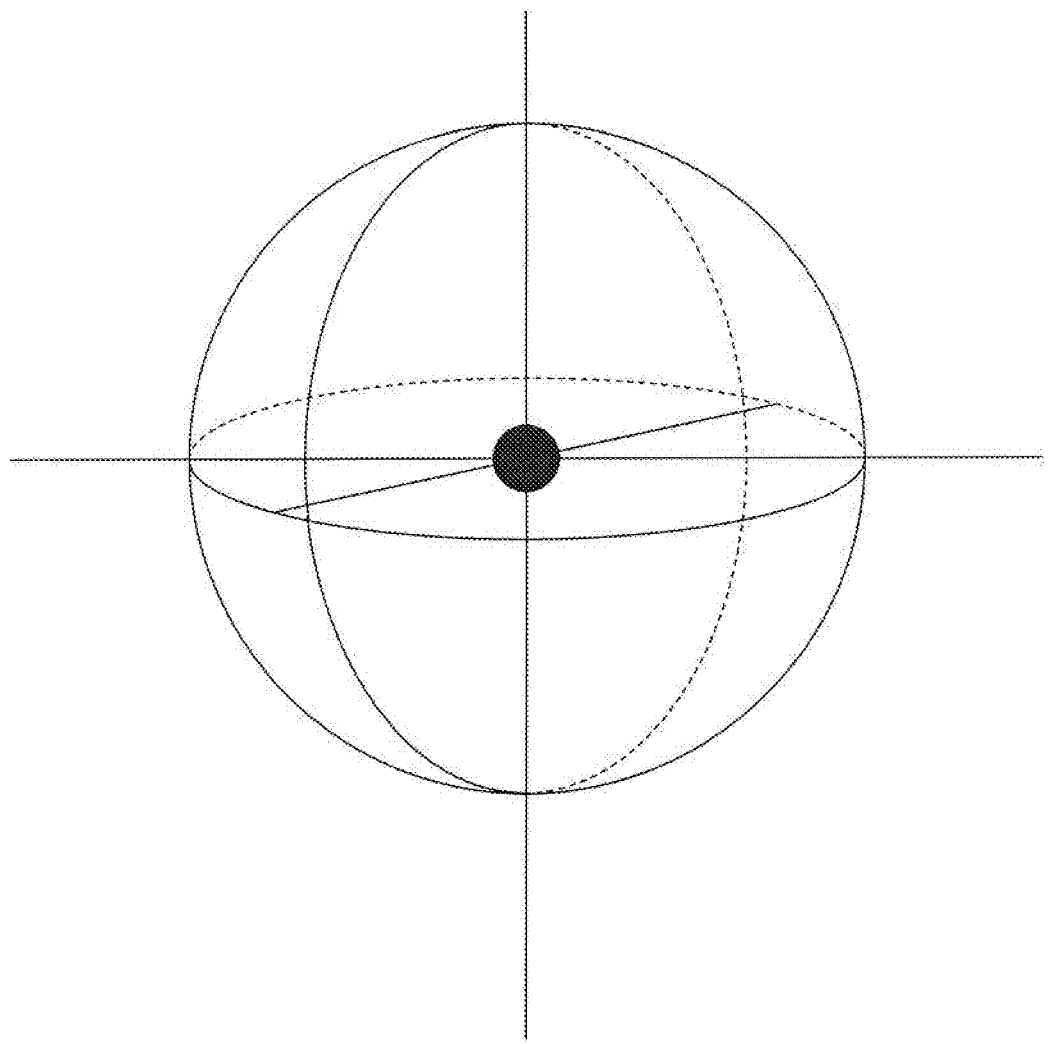
Figure 1D:
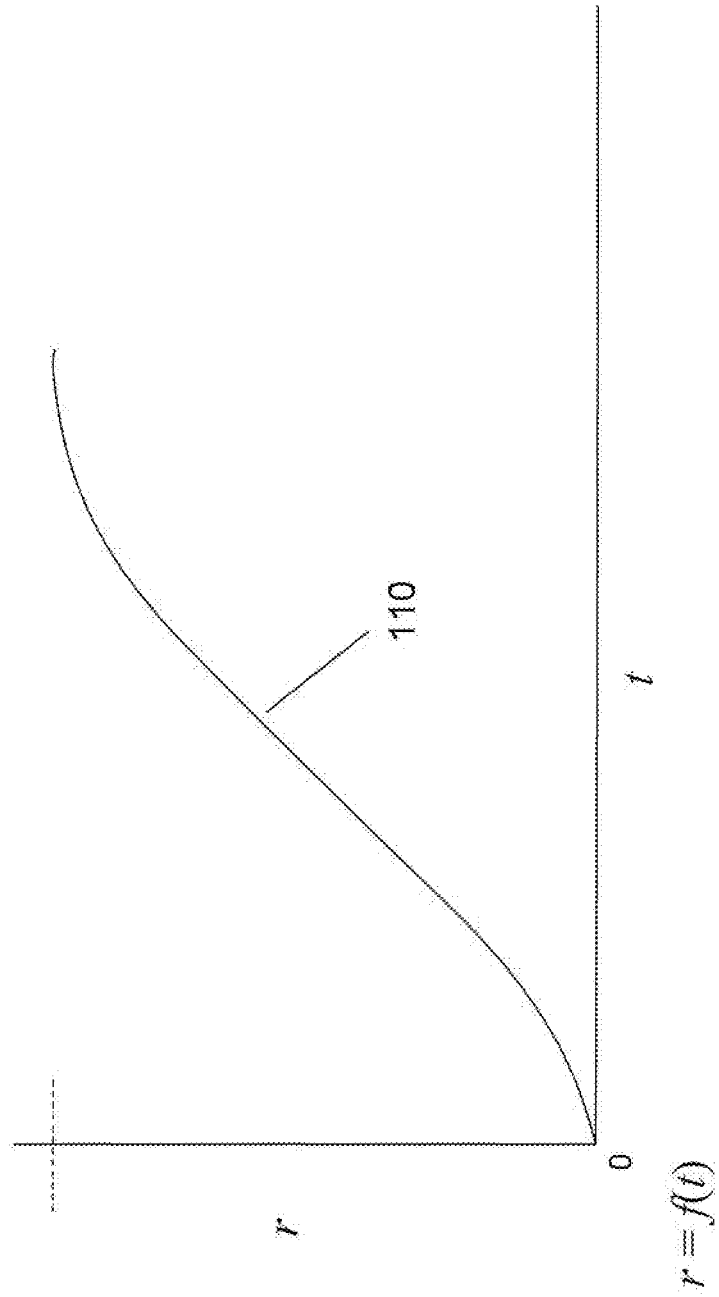

FIGS. 1A-D illustrate a simplistic computational model for tumor growth. In FIG. 1A, a small, nascent tumor 102 is located within a larger volume of tissue 104, with the location of the nascent tumor 102 located at the origin of a three-dimensional Cartesian coordinate system. The tumor is modeled as growing in a spherically symmetric manner, illustrated in FIGS. 1A-C, with the radius of the tumor increasing over time. A plot of the tumor radius versus time, as shown in FIG. 1D, would generally provide a curve 110 to which a computational model is fit to generate the radius as a function of time: r=ƒ(t). Unfortunately, a simplistic computational model, such as that described above with reference to FIGS. 1A-D, would almost certainly not provide sufficient accuracy to inform medical decisions. Tumors generally do not grow in a spherically symmetric fashion. Moreover, tumors in different patients, or at different locations within a patient, may grow at different rates. Tumors are also frequently not located at a central position within a spherical volume of tissue, and may be constrained by the geometry of the tissue within which they grow. For all of these reasons, and for many additional reasons, a more complex computational model for tumor growth is needed for medical applications.

Figure 2A:
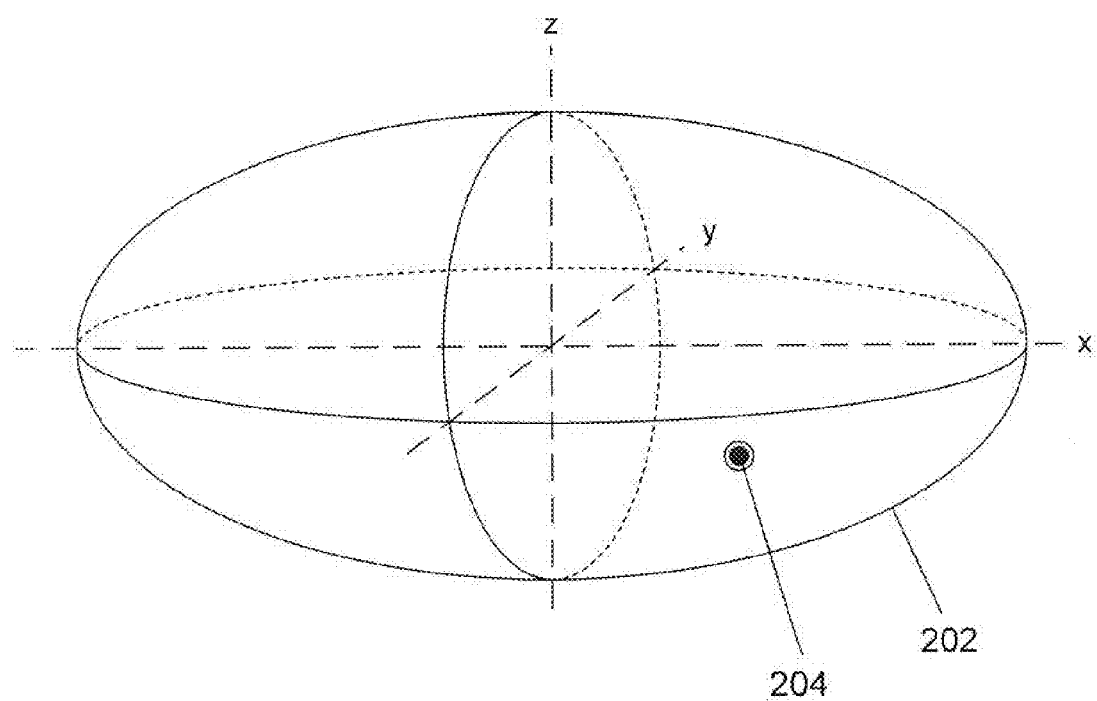
FIGS. 2A-C illustrate aspects of a more general computational model for tumor growth, employed by embodiments of the present invention.
Figure 2B:
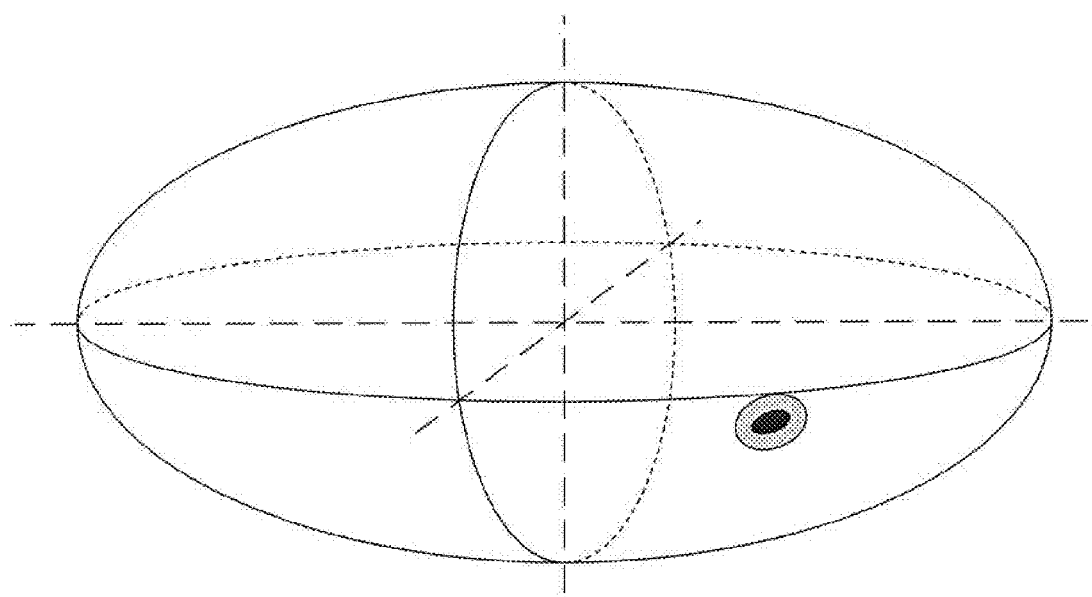
Figure 2C:
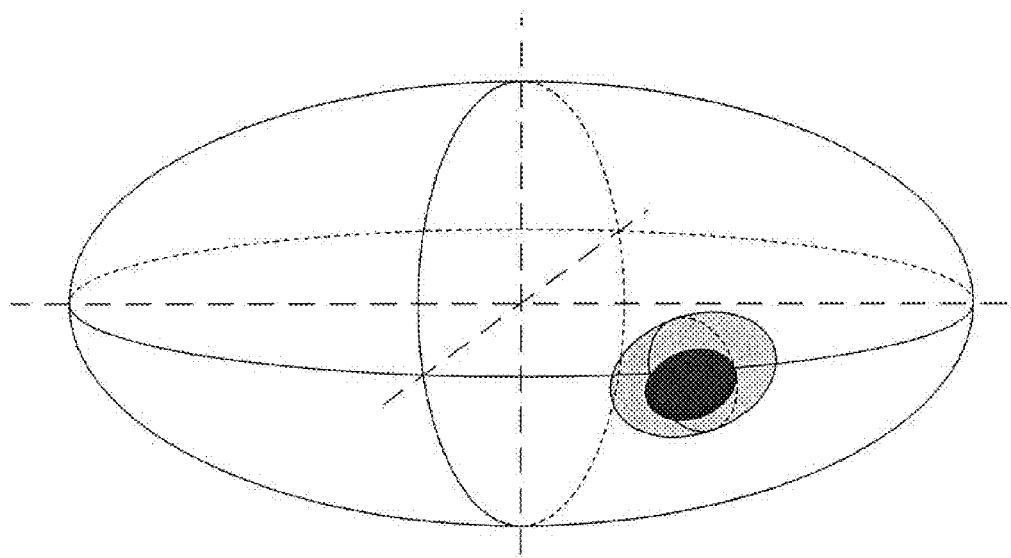

FIGS. 2A-C illustrate aspects of a more general computational model for tumor growth, employed by various embodiments of the present invention. First, the tissue within which the tumor grows may have an arbitrary geometry, such as the ellipsoid 202 volume of tissue shown in FIG. 2A. Although an ellipsoid has a high degree of symmetry, including an n-fold and two 2-fold symmetry axes coincident with the x, y, and z axes in FIG. 2A, arbitrary volumes, including low-symmetry volumes, can be accommodated by the computational models used in various embodiments of the present invention. Second, the nascent tumor 204 may be located arbitrarily within the volume of tissue, according to computational models employed in various embodiments of the present invention. As shown in the series of FIGS. 2A-C, the tumor may grow in a non-spherically symmetric fashion.

Figure 3A:
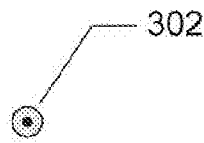
FIGS. 3A-D illustrate growth of a glioblastoma, each figure representing a two-dimensional cross-sectional slice through the tumor mass.
Figure 3B:
Figure 3C:
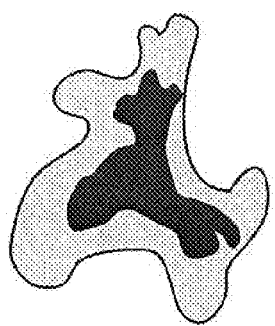
Figure 3D:
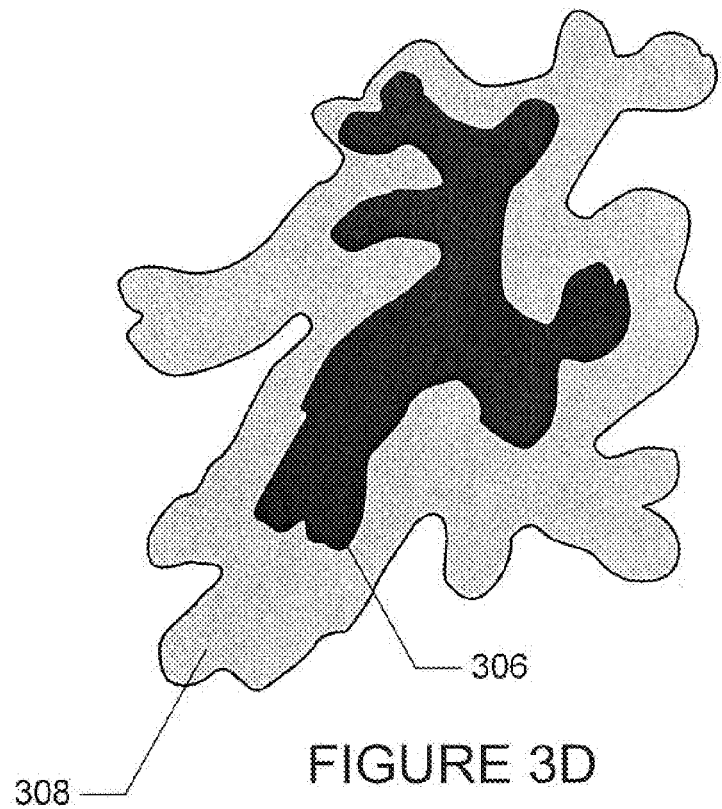

FIGS. 3A-D illustrate growth of a glioblastoma, each figure representing a two-dimensional cross-sectional slice through the tumor mass. Initially, as shown in FIG. 3A, the nascent tumor is small and roughly spherical 302. However, as shown in FIGS. 3B-D, as the tumor grows, both an internal necrosis-containing region 306 and an outer, edema-associated region 308 have an increasingly complex and low-symmetry shape. These complex, low-symmetry tumor volumes are a product of the inherent anisotropy biological tissues. Often, for example, tumor cells may migrate preferentially along vascular tissue or other internal boundaries, which may have complex geometries. Many other types of anisotropy occur in biological tissues. In brain tissue, for example, the distribution of white matter and gray matter is anisotropic, and the rate of glioma-cell migration may differ in the two different types of tissues.

A number of different processes contribute to tumor growth and spatial expansion. One process driving tumor growth is the proliferation of tumor cells, which generally divide, or proliferate, at rates that far exceed the normal proliferation rates of non-cancerous cells. FIGS. 4A-D illustrate a cell-proliferation component of tumor growth. FIG. 4A shows a cross-section of a small volume of tissue containing mostly normal cells, such as normal cell 402, represented by unfilled disks, and a single malignant cell 404, represented by a filled disk. Over time, as illustrated in the sequence of FIGS. 4A-C, the malignant cell divides to create progeny cells, and progeny cells, in turn, divide to produce a final, relatively high concentration of malignant cells within the volume of tissue, as shown in FIG. 4C. Often, there is a maximum concentration of malignant cells, k, at which point further malignant-cell proliferation ceases and necrosis ensues. A simple differential-equation model for the cell proliferation illustrated FIGS. 4A-C is:

$$\frac{\partial c}{\partial t} = \rho c \left(1 - \frac{c}{k}\right)$$

where
  c=the concentration of malignant cells at points in a tissue volume, and is therefore a scalar function over a bounded Cartesian space (x, y, z) and time;
  t=time;
  k=maximum malignant-cell concentration; and
  ρ=a net rate of malignant-cell proliferation.
Solution of this differential equation produces a function c(x, y, z, t) exponential in t. FIG. 4D plots a solution for this differential equation as a concentration of malignant cells, c, with respect to time, t. The concentration initially increases exponentially and then asymptotically approaches the maximum concentration in the malignant cells k.

Figure 5A:
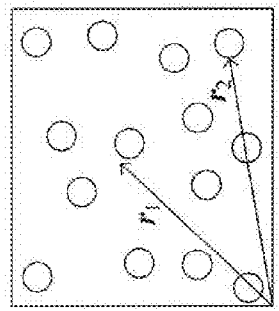
FIGS. 5A-D illustrate diffusive migration of tumor cells within a tissue.
Figure 5B:
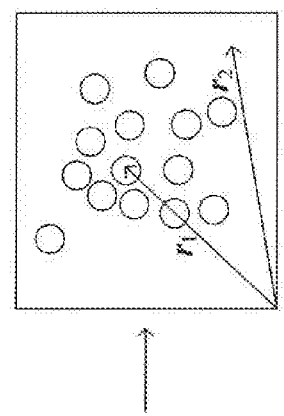
Figure 5C:
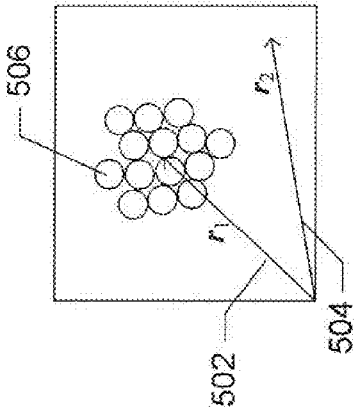
Figure 5D:
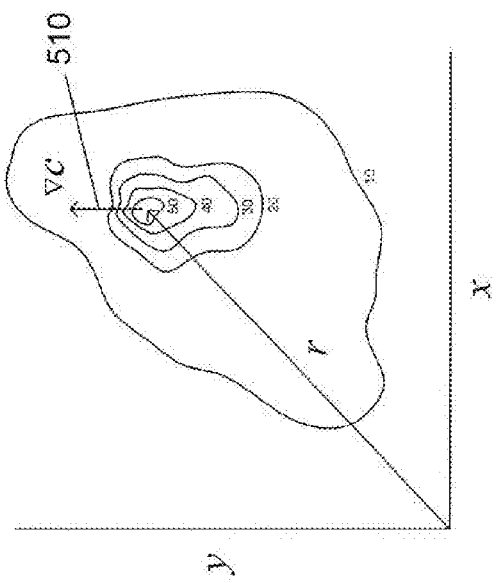

Another process that contributes to tumor growth is tumor-cell migration, which can be represented as a diffusion process. FIGS. 5A-D illustrate diffusive migration of tumor cells within a tissue. FIGS. 5A-C illustrate a small cross-section of a small volume of tissue containing tumor cells. In each of these figures, two positions within the volume are represented by position vectors $r_1$ 502 and $r_2$ 504. In FIG. 5A, the tumor cells, represented as unfilled disks, such as tumor cell 506, are clumped together in a small, central portion of the cross-section of the small volume of tissue. Over time, as represented by the series of FIGS. 5A-C, the cells migrate randomly, ending up, in FIG. 5C, relatively widely dispersed throughout the small volume of tissue. Note that, in the diffusive migration process, the concentration of malignant cells, c, decreases over time at position $r_1$, but increases over time at position $r_2$. In the computational modeling of diffusion processes, the direction of a gradient vector computed at a point (x, y, z), or $\vec{r}$, determines, for a next short interval of time, whether the concentration increases or decreases, due to diffusion, and the magnitude of the gradient vector is related to flux of diffusing entities, for a next short interval of time. For example, FIG. 5D shows a topographic-map-like plot of concentration within a two-dimensional cross-section of a tissue, where the concentrations are plotted using contour lines of constant concentration. Thus, FIG. 5D shows a three-dimensional concentration surface above the x,y plane, where the concentration of malignant cells c=ƒ(x,y). The differential operator $\nabla$ can be applied to a scalar function to produce a vector field, generating a gradient vector emanating from each point upon which the scalar function is defined. In the plot shown in FIG. 5D, for example, the gradient vector (g=$\nabla$c) 510 at position $\vec{r}$, points in the direction of the steepest concentration decrease.

To model the diffusive migration process, the concentration of malignant cells is assumed to be a scalar function of location and time:

$$c = f(x, y, z, t)$$
$$= f(r, t)$$

where x,y,z are Cartesian coordinates in three dimensions; and
  r is a three-dimensional positional vector.

The diffusive migration process can be expressed as a differential equation, indicating the rate of change of concentration of malignant cells, c, with time at each point in a spatial domain over which the scalar concentration function c is defined. One approach is to model the diffusive migration process as:

$$\frac{\partial c(r,t)}{\partial t} = D\nabla^2 c(r,t)$$

where

D is a constant diffusion coefficient over the entire domain of the concentration function;

$\nabla^2$ is the Laplacian operator; and c(r, t) is a scalar function of the concentration of malignant cells at position r at time t.

This provides a spherically symmetric diffusive migration, which, as discussed above, generally does not occur in anisotropic biological tissues. A second model is:

$$\frac{\partial c(r,t)}{\partial t} = \nabla \cdot (D(r)\nabla c(r,t))$$

where D(r) is a scalar diffusion coefficient that varies over the domain of the concentration function.

A third model employs a second-order-tensor field D to express the rate of diffusion in three dimensions from each position r within the domain of the concentration function:

$$\frac{\partial c}{\partial t} = \sum_{i=1}^{3} \sum_{j=1}^{3} \frac{\partial}{\partial x_i}\left(D_{ij}(r)\frac{\partial c}{\partial x_j}\right)$$

where D(r) is a tensor field.

One computational model used in embodiments of the present invention for tumor growth is a differential equation with a cell-proliferation component and a diffusive-migration component:

$$\frac{\partial c}{\partial t} = \nabla \cdot (D(r)\nabla c) + \rho c\left(1 - \frac{c}{k}\right)$$

where

D(r) is either a scalar function of position or a tensor field, as discussed above;

k is the maximum concentration of malignant cells obtained in the tissue; and

ρ is a rate of malignant-cell proliferation.

There is no closed-form solution to this equation. Instead, numerical solutions are computationally generated by numerical-analysis methods. This computational model is referred to as the diffusive-migration/bounded-exponential-cell-proliferation model ("DM/BECP model"). The cell proliferation component is bounded by the maximum-concentration constraint, discussed above, and incorporated in the proliferation component. The rate of change of the concentration of malignant cells with time may be expressed in various different units, such as the number of cells per $mm^3$ per day, month, or year, with appropriate units used for the diffusion coefficient, cell-proliferation constant, and maximum malignant-cell concentration. The model is further constrained by:

r∈B c(r,t=0)=c(r₀)

n·∇c=0 on ∂B

These constraints include: (1) the position at which the malignant-cell concentration is given by solution to the differential equation is within the volume of a particular tissue, B; (2) there is an initial malignant-cell concentration c(r₀) at each point r; and (3) there is no migration of malignant cells to points external from the volume of the tissue.

The DM/BECP model is related to various other computational models used to modeling various other problem domains. One such computational model is the Fisher-Kolmogorov equation initially used to describe the advancement of advantageous genes through a population. The DM/BECP model for tumor growth, the Fisher-Kolmogorov equation, and other such equations are known to have a traveling-wave solution, in the case of spherical spatial symmetry, in which a concentration wave expands radially outward from an initial central point with a constant velocity v equal to:

$v = 2\sqrt{D\rho}$

FIGS. 6A-F illustrate tumor growth, in cross-sections through a tumor volume, as monitored by two different types of medical imaging. A glioblastoma is assumed in the example of FIGS. 6A-C. As discussed above, the glioblastoma has a central, necrotic region 602 and an enclosing endemic region 604. The boundary of the internal, necrotic region is detected by T1-Gd-MRI ("T1") imaging while the boundary of the endemic region 604 is detected by T2-MRI ("T2") imaging. FIGS. 6A-C show the growth of both regions within the tumor over time. Note that, in general, diffusive invasion of tumor cells extends past the T2-imaging-detected boundary. FIG. 6D shows a plot of malignant-cell concentration over time along a line x (606 in FIG. 6A) through the cross-section of the tumor shown in FIGS. 6A-C. The concentration curve for FIG. 6A is shown as a solid line 610, the concentration curve for FIG. 6B is shown as a first dashed line 612, and the concentration curve for FIG. 6C is shown as a second dashed line 614. The horizontal dashed line 616 shows the concentration threshold for T1-imaging detection and the horizontal line 618 shows the concentration threshold for T2-imaging detection, respectively. These concentrations are designated $t_1$ 620 and $t_2$ 622. As shown in FIG. 6D, the concentration curves at each point in time form a concentration-gradient wave front which moves outward in both the positive and negative directions from the x=0 central point of the tumor 624. For any curve representing the concentration gradient at a particular time point, as shown in FIG. 6E, the x coordinate for the wave front, $x_{WF}$, may be computed as the x coordinate of a point 630 midway between the point of intersection of the concentration curve with the horizontal $t_1$ and $t_2$ threshold concentration lines. The positive-wave-front coordinate, $x_{WF}$, is plotted versus time, in FIG. 6D, for tumor growth represented in FIGS. 6A-C as modeled by the DM/BECP model of the present invention. The position of the wave front varies linearly with time, with the slope of the plotted line equal to the constant wave-front velocity $2\sqrt{D\rho}$. In fact, the wave-front velocity may initially be non-linear, but approaches linearity with increasing time.

The DM/BECP model, used in certain embodiments of the present invention, has been shown to accurately predict tumor growth for glioblastomas and other gliomas, and may, in addition, be applicable to a wide variety of other types of tumors and growths within normal tissues. However, the model is parameterized, with parameters ρ and D(r). These two parameters are tumor/patient specific. Thus, values for these parameters need to be obtained in order to use the DM/BECP model to characterize a particular tumor. As discussed above, assuming a constant diffusion coefficient D, the solution for the DM/BECP-model differential equation exhibits a constant-velocity concentration wave front. Using two different medical images of a tumor, obtained at two different times $t_1$ and $t_2$, the velocity of the concentration wave front is determined by:

$$v = \frac{x_{WF(t_2)} - x_{WF(t_1)}}{t_2 - t_1}$$

The wave fronts may be computed as equivalent radii of a spherical tumor of volume equal to the volumes of the tumor at times $t_1$ and $t_2$, using a threshold tumor cell concentration or other metric to determine the tumor boundary in the images. Alternatively, an average linear rate of expansion of the tumor along directions normal to surface of the tumor is computed as the wave-front velocity. Thus, two different MRI images are used to obtain one equation for the two unknown parameters D and $\rho$:

$$2\sqrt{D\rho} = \frac{x_{WF(t_2)} - x_{WF(t_1)}}{t_2 - t_1}$$

A second equation relating the two unknown parameters $\rho$ and D is needed in order to determine values for the parameters $\rho$ and D. An analytical solution for the differential equation $$\frac{\partial c}{\partial t} = D\nabla^2 c + \rho c$$

in spherical symmetry with a point-source initial condition on an infinite domain is known. From this analytical solution, an equation for the ratio of $\rho$ to D is derived as:

$$\left(\frac{\rho}{D}\right)_c = \left[\frac{4\ln\left(\frac{t_1}{t_2}\right)}{(T2r_{eqv})^2 - (T1r_{eqv})^2}\right]\left[\left[\frac{T1r_{eqv}^2 \ln\left(\frac{t_1}{t_2}\right)}{(T2r_{eqv})^2 - (T1r_{eqv})^2}\right] +\right.$$

$$\left.\ln\frac{t_1 k}{N_0}\left[\frac{\Pi(T2r_{eqv}^2 - T1r_{eqv}^2)}{\ln\left(\frac{t_1}{t_2}\right)}\right]^{3/2}\right]$$

where $T1r_{eqv}$ and $T2r_{eqv}$ are the radii of the equivalent, spherical tumor volumes corresponding to the T1-imaging and T2-imaging tumor volumes, respectively;

$t_1$ and $t_2$ are the threshold concentrations for T1-imaging and T2 imaging, respectively, k is the maximum malignant-cell concentration; and $N_0$ is an initial malignant-cell concentration or number.

The ratio $$\frac{\rho}{D}$$

computed from the above equation, with k and $N_0$ assumed to be constants, $$\left(\frac{\rho}{D}\right)_c = f_{analytical}(T1r_{eqv}, T2r_{eqv}),$$

is closely related to observed values for the ratio obtained from simulations using the DM/BECP model, $$\left(\frac{\rho}{D}\right)_0 = \text{model-simulation } (T1r_{eqv}, T2r_{eqv}).$$

Figure 7A:
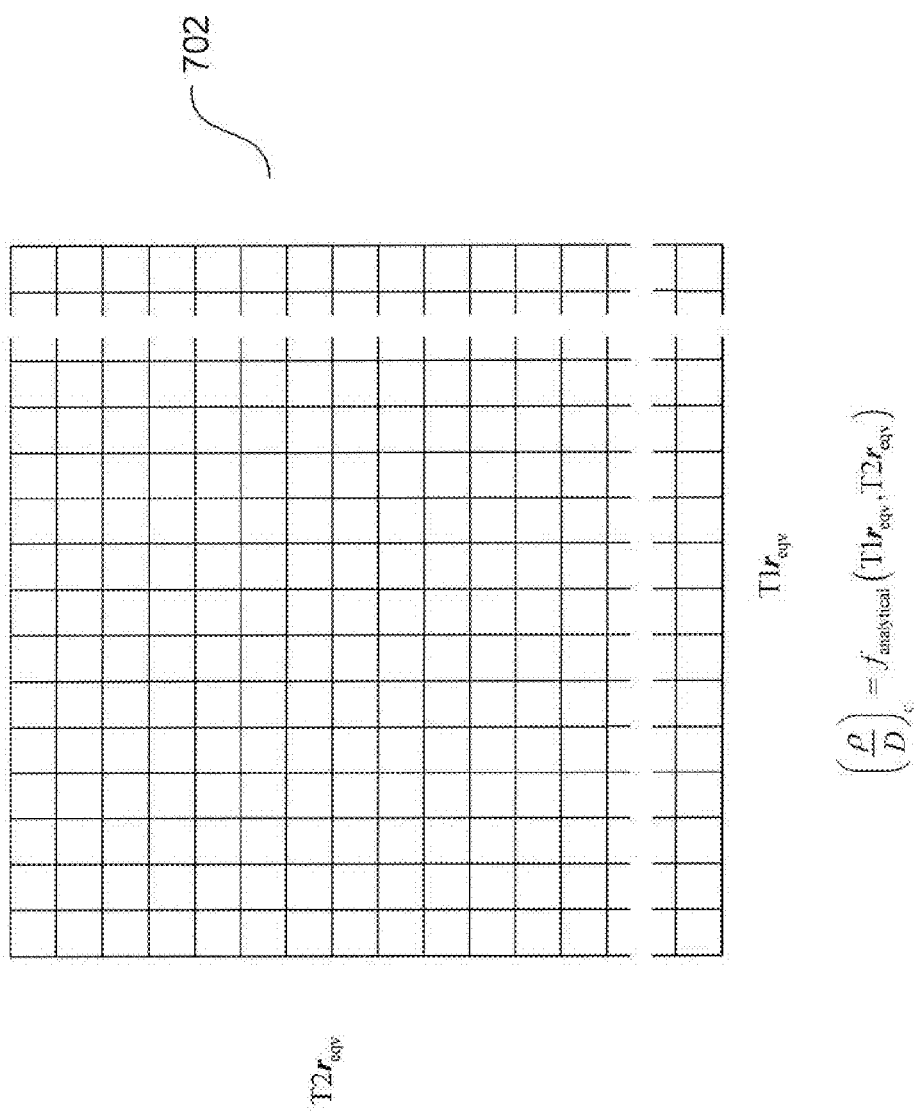
FIGS. 7A-D illustrate preparation of a lookup table from which corrections to computed $$\frac{\rho}{D}$$
Figure 7B:
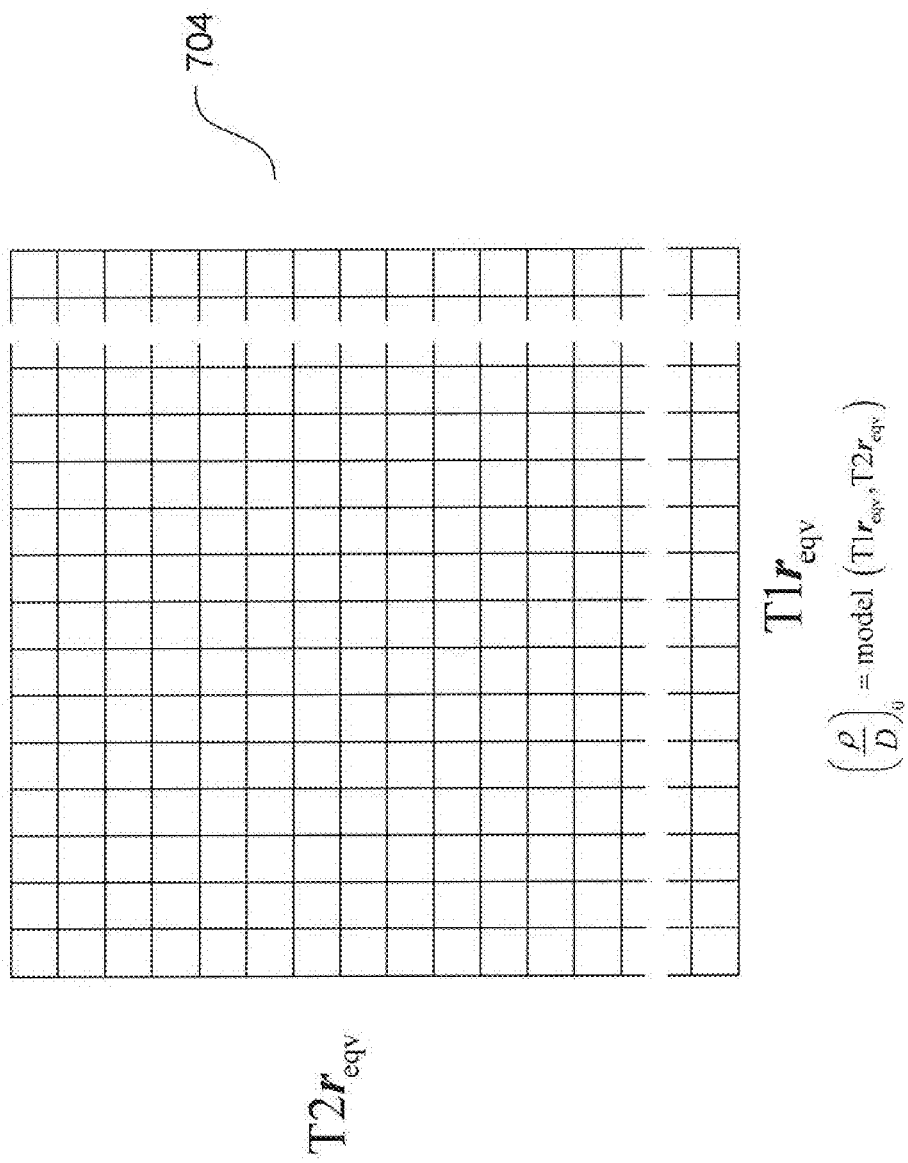

FIGS. 7A-D illustrate preparation of a lookup table from which corrections to computed $$\frac{\rho}{D}$$

values are obtained according to one embodiment of the present invention. As shown in FIG. 7A, the analytical solution for the differential equation $$\frac{\partial c}{\partial t} = D\nabla^2 c + \rho c$$

is used to derive an analytical function for computing $$\left(\frac{\rho}{D}\right)_c, \left(\frac{\rho}{D}\right)_c = f_{analytical}(T1r_{eqv}, T2r_{eqv}),$$

where $T1r_{eqv}$ is the radius of a spherical volume equivalent to the volume of the inner, necrotic portion of the glioblastoma, as measured by T1-imaging, and $T2r_{eqv}$ is the radius of the spherical volume equivalent to the total tumor volume, as measured by T2-imaging. The additional parameters k and $N_0$ are treated as constants. Thus, as shown in FIG. 7A, a table of $$\left(\frac{\rho}{D}\right)_c$$

values are computed by the analytical function for various $T1r_{eqv}$ and $T2r_{eqv}$ values, and included in a table 702. Similarly, as shown in FIG. 7B, an additional table 704 of observed values $$\left(\frac{\rho}{D}\right)_0$$

are prepared by DM/BECP-model-based simulations of tumor growth, where $$\left(\frac{\rho}{D}\right)_0 = \text{model-simulation } (T1r_{eqv}, T2r_{eqv}).$$

Figure 7C:
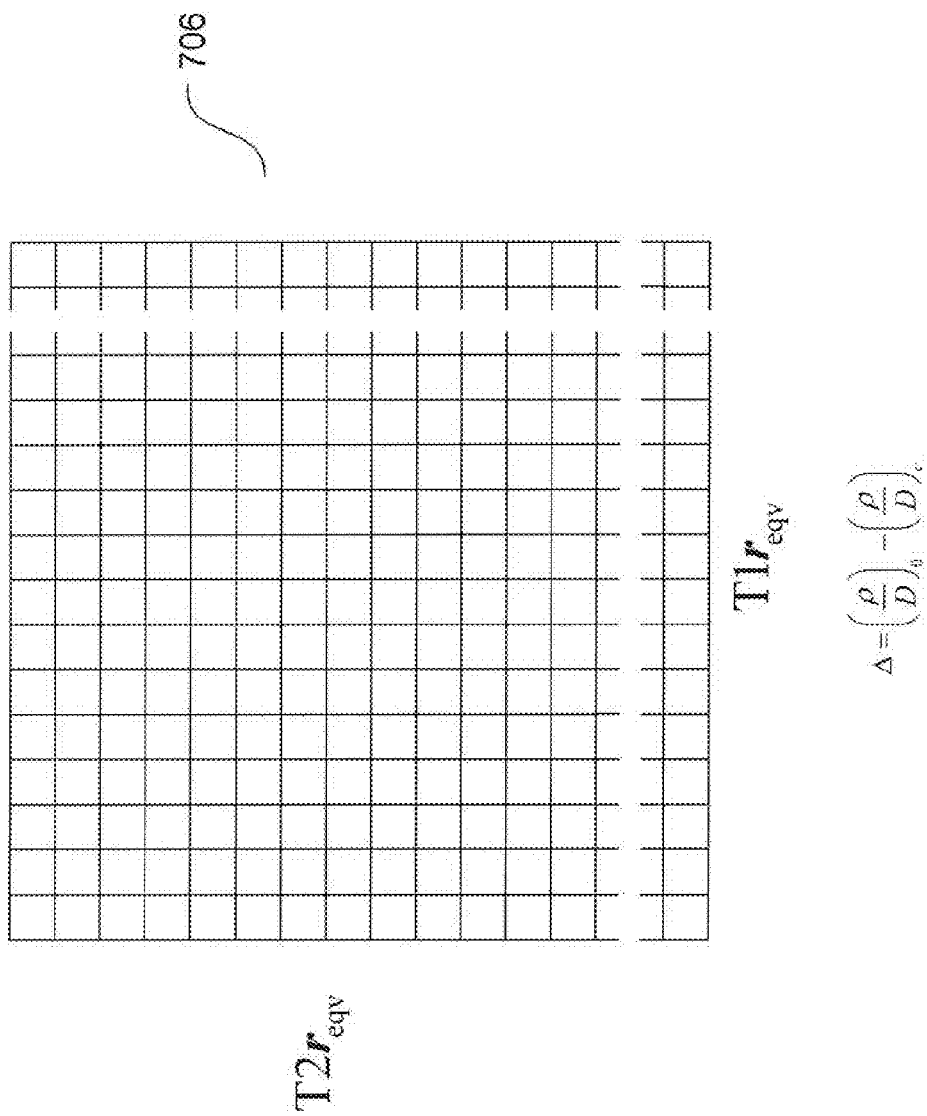
Figure 7D:
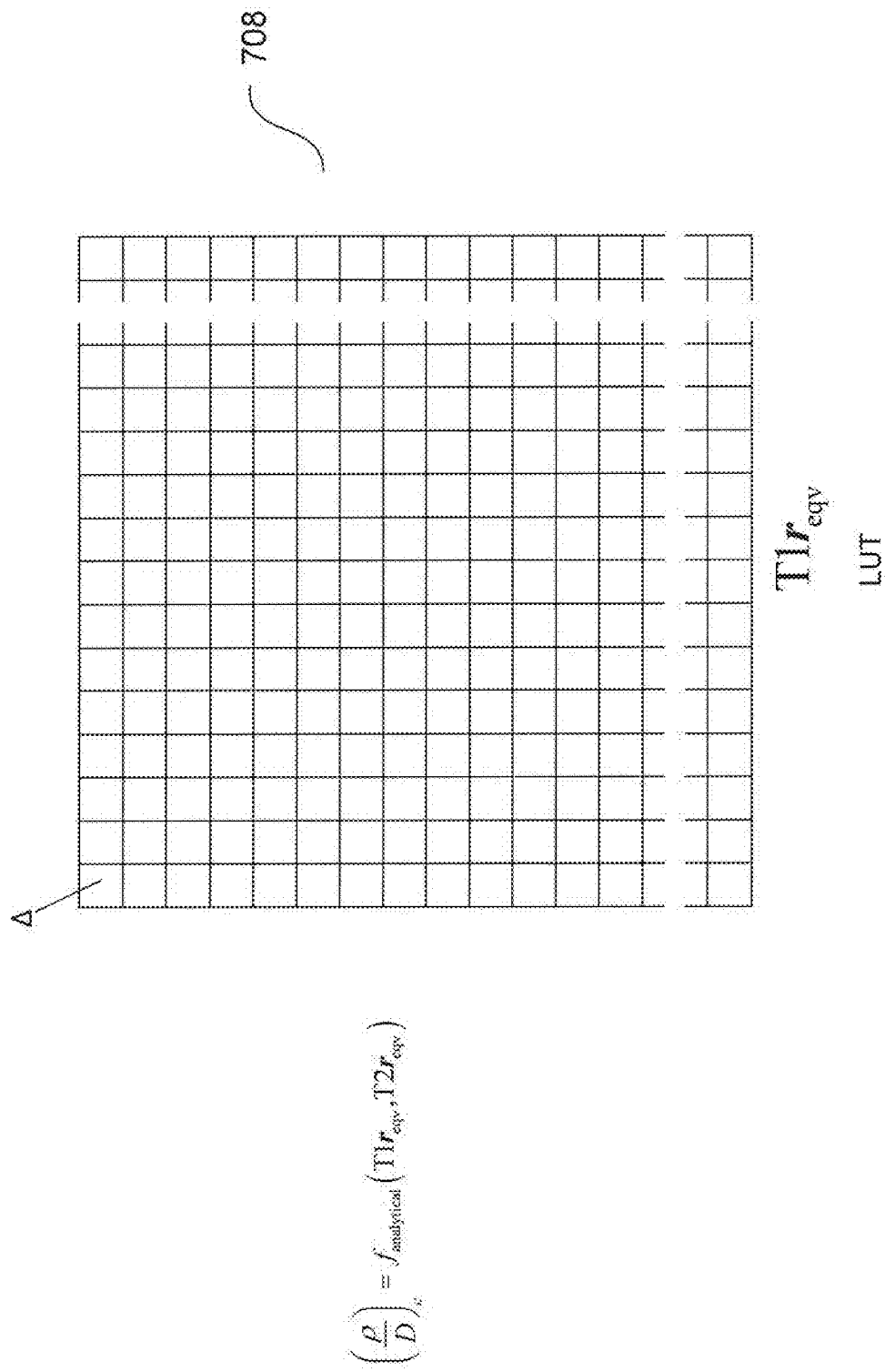

As shown in FIG. 7C, a table 706 of corrections, or Δ values, $$\Delta = \left(\frac{\rho}{D}\right)_0 - \left(\frac{\rho}{D}\right)_c,$$

is prepared from tables 702 and 704 by each value in table 702 from the corresponding value in table 704, as shown in FIG. 7C. Finally, as shown in FIG. 7D, a lookup table ("LUT") is prepared from table 706, shown in FIG. 7C, by rearranging the table, so that, in the rearranged table, the Δ values are indexed by $$\left(\frac{\rho}{D}\right)_c$$

and $T1r_{eqv}$.

Once the LUT (708 in FIG. 7D) is prepared, as discussed above, then an estimated observed $$\frac{\rho}{D}$$

value, $$\left(\frac{\rho}{D}\right)_0,$$

is obtained from estimates of $T1r_{eqv}$ and $T2r_{eqv}$ computed from a T1 and a T2 image, by:

$$\left(\frac{\rho}{D}\right)_0 = LUT\left(\left(\frac{\rho}{D}\right)_c, T1r_{eqv}\right) + \left(\frac{\rho}{D}\right)_c$$

This provides the second equation relating the two unknown parameters D and ρ. With two equations for the two unknowns, values for ρ and D are computed by, for example:

$$\frac{\rho}{D} = x_1$$
$$2\sqrt{D\rho} = x_2$$
$$2\sqrt{D^2 x_1} = x_2$$
$$D = \frac{x_2}{2\sqrt{x_1}}$$
$$\rho = \frac{x_2\sqrt{x_1}}{2}$$

where $x_1$ and $x_2$ are numeric values computationally obtained from images, as discussed above.

With numerical values for D and ρ obtained as discussed above, a complete computation model for a particular tumor/patient are numerically generated. Thus, for example, a tumor volume can computed for a malignant-cell concentration threshold $t_3$ lower than either $t_1$ or $t_2$ for performing various treatment plans. In addition, the ratio $$\frac{\rho}{D}$$

characterizes the aggressiveness of a particular tumor. Thus, the ratio $$\frac{\rho}{D}$$

can help to determine the prognosis for a patient, as well as to better inform treatment selection and treatment planning. Other characteristics of the tumor may be derived from various expressions derived from the diffusive-migration/exponential-cell-proliferation model.

FIG. 8 illustrates the complex, three-dimensional nature of the imaging and model-parameter-estimation problems associated with obtaining a patient-specific model for glioblastoma growth, according to embodiments of the present invention. In FIG. 8, a Cartesian coordinate system 802 is superimposed onto a cutaway illustration of a glioblastoma within a patent's cranium. In FIG. 8, three partial cross-sections 804-806 of a glioblastoma tumor are shown with respect to three mutually orthogonal planes defined by the positive x, y, and z axes. The tumor has a convoluted, irregular surface with many protrusions and invaginations. Those familiar with biological imaging and computing would immediately recognize that even the relatively straightforward task of placing two different images, taken at two different times, of the tumor into a common coordinate system, given a generally irregular and complex tumor expansion, represents an exceedingly tedious and difficult task that can feasibly be undertaken only by computational methods. The spatial registration task requires methodically exploring many different relative orientations of the two different images to determine a relative orientation that, in part, minimizes the spatial difference, computed in three dimensions, between two different tumor surfaces under various orientation constraints that may be available from imaging parameters. Such spatial registration tasks require millions of computations. Other tasks, including computing tumor-expansion velocities, ρ/D values, D tensor fields or D(x,y,z) scalar fields are also computationally complex, and cannot be feasibly undertaken by any means other than computation on an electronic computer. It is not possible to compute these characteristics and parameters accurately by hand, in any time frame, and quite impossible to carry out the millions of calculations needed to compute these characteristics and parameters in reasonable and feasible time frames needed for medical prognosis, diagnosis, and treatment planning.

Figure 9A:
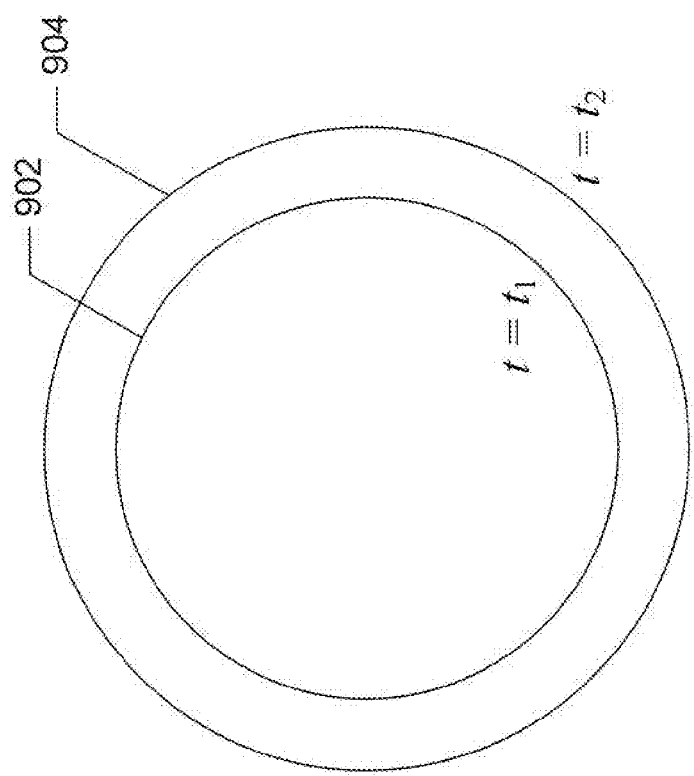

FIGS. 9A-E illustrate one method by which the scalar diffusion field D(r) is determined. The method illustrated in FIGS. 9A-E is but one example of various methods that are employed in order to determine the D(r) scalar field. As shown in FIG. 9A, two images of a tumor are obtained at different times $t_1$ and $t_2$. In FIG. 9A, the tumor is shown as disk-shaped, idealized cross-sections, where an inner disk region 902 represents a cross-section through the tumor volume at time $t=t_1$ and disk-shaped region 904 represents a cross-section through the tumor volume at time $t=t_2$. A three-dimensional grid, assumed in the current discussion to be a lattice with cubic unit cells, is superimposed over the region of tumor expansion 906 lying between the surface of the tumor at time $t=t_1$ 902 and the surface of the tumor at time $t=t_2$ 904, as shown in two-dimensional cross-section in FIG. 9B. Each three-dimensional cell within the three-dimensional grid is associated with two parameters κ and γ, where:

$$\kappa = \frac{\text{white-matter cells}}{\text{total cells}}$$

$$\gamma = \frac{\text{gray-matter cells}}{\text{total cells}}$$

The relative numbers of white-matter cells κ and gray-matter cells γ for each grid element is obtained from the $t=t_1$ image by various image-analysis techniques, or by use of the $t=t_1$ image along with generalized models of the distribution of white-matter and gray-matter cells within the brain.

Figure 9C:
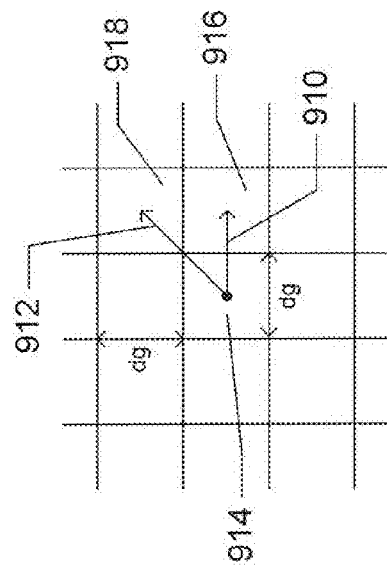
Figure 9D:
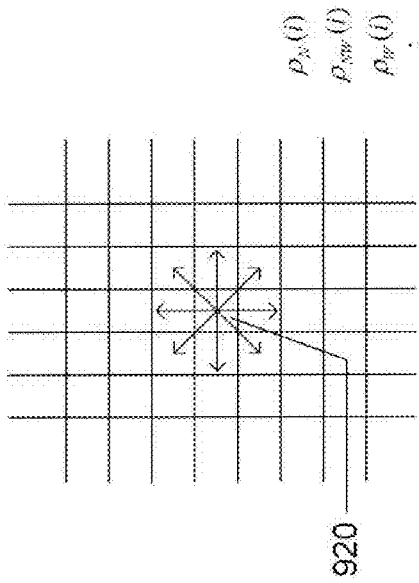
Figure 9B:
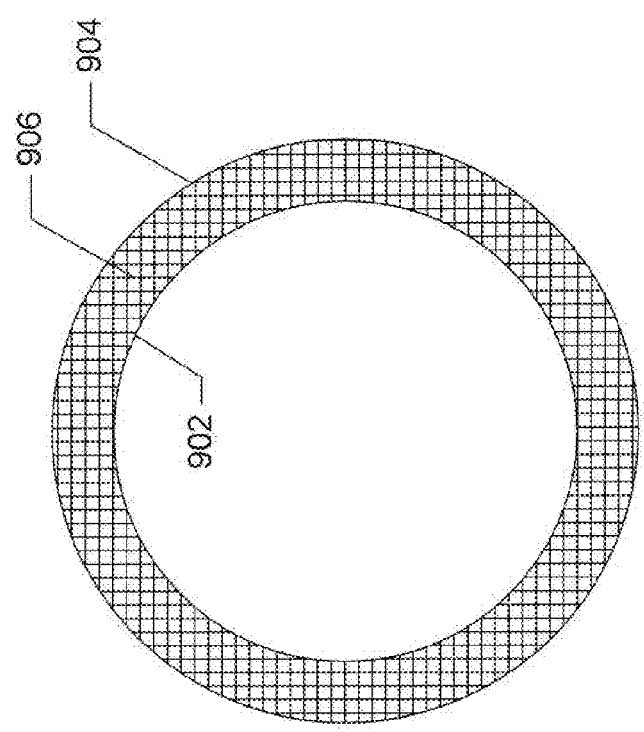

In the determination of the scalar diffusion-coefficient field, various paths are constructed between points on the surface of the $t=t_1$ volume and points on the surface of the $t=t_2$ volume. The paths are constructed as a sequence of adjacent grid elements, each pair of consecutive grid elements in a path sharing at least one common point in the three-dimensional grid, with the first grid element in a path lying on the $t=t_1$ surface and the final element in a grid-element path lying on the $t=t_2$ surface. FIG. 9C shows, in cross-section, two different possible subpaths 910 and 912 leading from a first grid element 914 to one of two second grid elements 916 and 918, respectively. The length of a subpath that includes grid elements 914 and 916 is equal to $d_g$, the grid spacing, whereas the length of a subpath that includes grid elements 914 and 918 is $\sqrt{2}d_g$. As shown in FIG. 9D, there is a probability associated with each pair of grid elements that include a given grid element i 920 and each of the surrounding grid elements that share at least one point with grid element i for inclusion as a next subpath in a sequence of grid elements that represents a path from the surface of the $t=t_1$ volume and the surface of the $t=t_2$ volume. In other words, at each point in the three-dimensional grid, a probability $P_{i,j}$ is calculated for a tumor surface to expand in any of 26 different directions from grid element i to an adjacent grid element j. Eight of the directions, shown in FIG. 9D, are planar, with an additional nine directions leading to grid elements below the plane of grid element i and an additional nine directions leading to grid elements above the plane of grid element i.

The method for determining the scalar diffusion-coefficient field assumes that the velocity of tumor expansion, at each point in time and small volume of space, is a linear combination of a velocity $V_w$ in white matter and a velocity $V_g$ in gray matter, with contributions of velocities $V_w$ and $V_g$ proportional to the relative amounts of white matter and gray matter in the small volume:

$$V = \kappa V_w + \gamma V_g$$

Figure 9E:
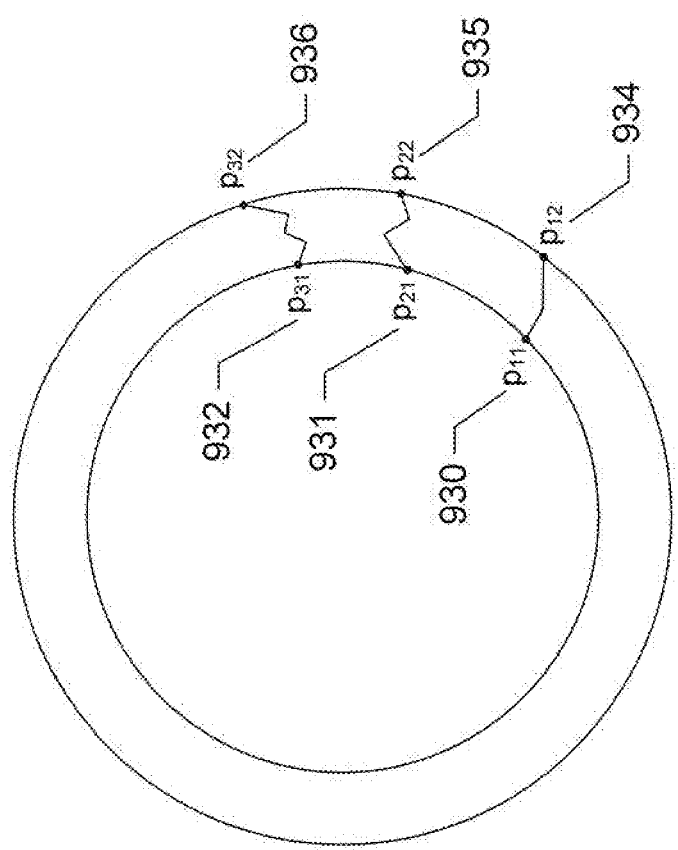

As shown in FIG. 9E, the current method selects a large number of points coincident with the $t=t_1$ tumor surface, including points $p_{11}$, $p_{21}$ and $p_{31}$ 930-932 in FIG. 9E, and computes a most likely path to corresponding points on the $t=t_2$ surface of the tumor, shown in FIG. 9E as points $p_{12}$, $p_{22}$ and $p_{32}$ 934-936. The aggregate κ and γ values for a path p is computed as:

$$\kappa_p = \sum_{i=1}^{n} \kappa_i$$

$$\gamma_p = \sum_{i=1}^{n} \gamma_i$$

where there are n grid elements in the path. As discussed with reference to FIG. 9C, path-component length is computed between each two successive grid elements in a path as:

$$\text{path\_component\_length} = \begin{cases} \text{when planar diagonal,} & \sqrt{2}d_g \\ \text{when non-planar diagnonal,} & 1.73d_g \\ \text{otherwise} & d_g \end{cases}$$

The length of a path p is then:

$$\text{length}(p) = \sum_{i=1}^{n-1} \text{path\_component\_length}_i.$$

The velocity of tumor expansion along a given path p, $V_p$, is computed as:

$$V_p = \frac{\text{length}(p)}{t_2 - t_1}$$

From any grid element $j_1$ lying on the $t=t_1$ surface, there is a computable probability $P(j_1, j_2, \ldots j_n)$ that the tumor expands from grid element $j_1$ to grid element $j_n$ on the $t=t_2$ surface along the sequence of grid elements $j_1, j_2, \ldots j_n$:

$$P(j_1, j_2, \ldots, j_n) = f(P_{j_1,j_2}, P_{j_2,j_3}, \ldots, P_{j_{n-1},j_n})$$

The function $f()$ is computed in various ways, including combining the probabilities of tumor expansion between adjacent grid-element path components in ways that consider the κ and γ values for the grid elements in the path, the distance of the grid elements from $t=t_1$ surface, and other parameters. Assuming a computable function $f()$, the paths between each grid element m on the $t=t_1$ surface to a corresponding grid element n on the $t=t_2$ surface is computed as the path with maximum computed probability:

$$P_{m,n} = \max_{\text{all possible } j_1=m, j_2,\ldots, j_n=n} P(j_1, j_2, \ldots, j_n)$$

After computing paths from some well-distributed set of $t=t_1$ surface points to the $t=t_2$ surface, a set of paths $p_1, p_2, \ldots p_n$ is obtained. The velocities of tumor expansion for each path are then computed as:

$$\begin{bmatrix} \kappa_1 & \gamma_1 \\ \kappa_2 & \gamma_2 \\ \vdots & \vdots \\ \kappa_{n-1} & \gamma_{n-1} \\ \kappa_n & \gamma_n \end{bmatrix} \begin{bmatrix} V_w \\ V_g \end{bmatrix} = \begin{bmatrix} V_1 \\ \vdots \\ V_{n-1} \\ V_n \end{bmatrix}$$

This is an overdetermined set of equations that allows the velocities $V_w$ and $V_g$ to be computed by a least-squares regression or by other techniques for determining variable values in overdetermined systems of equations. Finally, the diffusion coefficients $D_w$ and $D_g$ are obtained by assuming a constant proliferation coefficient $\rho$ as follows:

$$D_w = \frac{V_w^2}{4\rho}$$

$$D_g = \frac{V_g^2}{4\rho}$$

For each grid element, a scalar diffusion coefficient is computed as a numeric combination of the diffusion coefficients $D_w$ and $D_g$ based on the $\kappa$ and $\gamma$ values for the grid element.

The DM/BECP model can be further expanded to take into account not only the heterogeneity of the brain tissue, but also its anisotropy, including facilitation of glioma cell migration in the direction of white matter fibers, as briefly mentioned above. The model is expressed as:

$$\frac{\partial c}{\partial t} = \nabla \cdot (D(x)\nabla c) + f(c),$$

where D is a diffusion tensor, at each point within a tissue, that describes tumor cell diffusion. The diffusion tensor is a 3-by-3 symmetric positive definite matrix that models the local anisotropy of the cell diffusion tensor. The expanded model takes into account both location and direction within the structure of the brain tissue, with proliferation $f(c)$ modeled by a logistic law with $c_m = 10^5$ cells/mm$^3$.

Initial conditions are defined as $c(x, t=0) = c_0(x)$ and, to inhibit migration of glioma cells outside of the brain tissue, $D(x)\nabla c \cdot n = 0$ for x on the sulcal and ventricular boundary of the brain, where n is the surface normal. The above model equation can be solved, to estimate tumor-cell density c, using 3D finite differences, which involves approximating temporal and spatial derivatives by their discrete expressions. First, the following PDE is solved:

$$\begin{cases} \frac{\partial c}{\partial t} = \nabla \cdot (D(x)\nabla c) + \rho c \\ c(x, t=0) = c_0(x) \end{cases}$$

where $c_0$ is the concentration of the tumor cells at t=0. Each part of this PDE is then discretized using $\Delta T$ as a time step and $(\Delta X, \Delta Y, \Delta Z)$ as space steps to obtain the following discrete equation, $$\frac{C^{n+1} - C^n}{\Delta T} = AC^n,$$

where $C^n$ is a vector representing cell density at the time $n\Delta T$ and A is a large sparse matrix representing discrete operators. This discrete equation represents the forward Euler method. Instead of using the forward Euler method, an alternative $\theta$-method is used in order to increase numerical stability. The $\theta$-method consists of combining forward and backward numerical schemes, as follows:

$$\frac{C^{n+1} - C^n}{\Delta T} = (1-\theta)AC^n + \theta AC^{n+1},$$

Denoting $\delta^n = C^{n+1} - C^n$, the cell concentration at time (n+1)$\Delta T$ is computed by first solving the equation $$(I - \theta \Delta TA)\delta^n = \Delta T A C^n,$$

where I is the identity matrix, which gives the value for $\delta^n$. The preconstrained gradient method is used to solve this large sparse system and obtain the tumor-cell concentration as $$C^{n+1} = C^n + \delta^n$$

Initial conditions are represented by a tumor-cell concentration $C^0$ in a manually-selected grid element. Using the notation $(\lambda_i, e_i)_{i=1,2,3}$ to denote the eigenvalues and eigenvectors of the water diffusion tensor D obtained by diffusion-tensor imaging ("DTI"). The following transformed tensor D is to represent the diffusion tensor of tumor cells:

$$\overline{D} = \overline{\lambda}_1(r)e_1e_1^T + \overline{\lambda}_2(r)e_2e_2^T + \overline{\lambda}_3(r)e_3e_3^T.$$

This operation modifies the eigenvalues of the tensor, but not the eigenvectors, which implies that the tensor orientation is preserved while the diffusion values along the principal axes and the anisotropy are changed. The transformation is controlled by a parameter r. When r equals 1, the tensor is not changed. r<1 corresponds to a decrease in anisotropy and r>1 to an increase in anisotropy.

The finite-differences method is next described. Let c(t,x) denote the cell concentration at time t and location x of the space. The expanded model equation can be expressed as:

$$\frac{\partial c}{\partial t} = \sum_{i,j=1}^{3} D_{ij} \frac{\partial^2 c}{\partial x_i \partial x_j} + \sum_{i=1}^{3} \tilde{D}_i \frac{\partial c}{\partial x_i} + \rho c,$$

where $$\tilde{D}_i = (D\nabla)i = \sum_{j=1}^{3} \frac{\partial D_{ij}}{\partial x_j}.$$

$\tilde{D}$ is derived from the tensor D by computing its element-by-element gradient. Let $c(n\Delta T, i\Delta X, j\Delta Y, k\Delta Z) = C_{i,j,k}^n$ and let $C^n$ denote the vectorized version of $C_{i,j,k}^n$. The following discrete schemes are used for computing the derivatives:

$$\frac{\partial c}{\partial t} \to \frac{C_{i,j,k}^{n+1} - C_{i,j,k}^n}{\Delta T}$$

$$\frac{\partial c}{\partial x} \to \frac{C_{i+1,j,k}^n - C_{i-1,j,k}^n}{2\Delta X}$$

$$\frac{\partial^2 c}{\partial x^2} \to \frac{C_{i+1,j,k}^n - 2C_{i,j,k}^n + C_{i-1,j,k}^n}{\Delta X^2}$$

$$\frac{\partial^2 c}{\partial x \partial y} \to \frac{C_{i+1,j+1,k}^n + C_{i-1,j-1,k}^n - C_{i+1,j-1,k}^n - C_{i-1,j+1,k}^n}{4\Delta X \Delta Y}$$

and similarly for $$\frac{\partial c}{\partial y}, \frac{\partial c}{\partial z}, \frac{\partial^2 c}{\partial y^2}, \frac{\partial^2 c}{\partial z^2}, \frac{\partial^2 c}{\partial x \partial z}, \text{ and } \frac{\partial^2 c}{\partial y \partial z}.$$

The following discrete model-equation expression for is then obtained:

$$\frac{C_{i,j,k}^{n+1} - C_{i,j,k}^n}{\Delta T} = D_{11}\frac{C_{i+1,j,k}^n - 2C_{i,j,k}^n + C_{i-1,j,k}^n}{\Delta X^2} +$$
$$D_{22}\frac{C_{i,j+1,k}^n - 2C_{i,j,k}^n + C_{i,j-1,k}^n}{\Delta Y^2} + D_{33}\frac{C_{i,j,k+1}^n - 2C_{i,j,k}^n + C_{i,j,k-1}^n}{\Delta Z^2} +$$
$$2D_{12}\frac{C_{i+1,j+1,k}^n + C_{i-1,j-1,k}^n - (C_{i+1,j-1,k}^n + C_{i-1,j+1,k}^n)}{4\Delta X \Delta Y} +$$
$$2D_{13}\frac{C_{i+1,j,k+1}^n + C_{i-1,j,k-1}^n - (C_{i+1,j,k-1}^n + C_{i-1,j,k+1}^n)}{4\Delta X \Delta Z} +$$
$$2D_{23}\frac{C_{i,j+1,k+1}^n + C_{i,j-1,k-1}^n - (C_{i,j+1,k-1}^n + C_{i,j-1,k+1}^n)}{4\Delta Y \Delta Z} +$$
$$\tilde{D}_1\frac{C_{i+1,j,k}^n - C_{i-1,j,k}^n}{2\Delta X} + \tilde{D}_2\frac{C_{i,j+1,k}^n - C_{i,j-1,k}^n}{2\Delta Y} +$$
$$\tilde{D}_3\frac{C_{i,j,k+1}^n - C_{i,j,k-1}^n}{2\Delta Z} + \rho C_{i,j,k}^n$$

which can be rewritten as $$\frac{C^{n+1} - C^n}{\Delta T} = AC^n,$$

where A is a big sparse matrix with 19 diagonal elements and where elements of A depend on D, $\tilde{D}$, $\rho$, and on the space/time discretization step sizes ($\Delta T, \Delta X, \Delta Y, \Delta Z$).

To fit the best solution, the parameters are chosen $\Delta T$ and $\theta$ with care. Neglecting the diffusion term, the following recursive scheme is obtained:

$$\frac{C^{n+1} - C^n}{\Delta T} = (1-\theta)\rho C^n + \theta \rho C^{n+1}$$

$$C^{n+1} = \frac{1 - \rho \Delta T \theta + \rho \Delta T}{1 - \rho \Delta T \theta} C^n$$

Denoting $u = \rho \Delta T$, the following solution for an initial condition $C^0$ is obtained:

$$C^n = \left(\frac{1 - \theta u + u}{1 - \theta u}\right)^n C^0.$$

The analytical solution for this exponential proliferation law is $C^n = C^0 e^{n\rho \Delta T}$, leading to the relation $$\left(\frac{1 - \theta u + u}{1 - \theta u}\right)^n = e^{nu},$$

which gives a relationship between the parameters $$\theta = \frac{1}{u} - \frac{1}{e^u - 1} = \frac{1}{\rho \Delta T} - \frac{1}{e^{\rho \Delta T} - 1}.$$

In this case, the diffusion D is zero.

The DM/BECP model, discussed above, can be expanded in various additional ways. As one example, the model can be expanded to include an additional term for the effects of radiation therapy:

$$\frac{\partial c}{\partial t} = \nabla \cdot (D\nabla c) + \rho c\left(1 - \frac{c}{k}\right) - Rc\left(1 - \frac{c}{k}\right)$$

where $$R(x, t, \text{Dose}(x,t)) \equiv \begin{cases} 0 & \text{for } t \notin \text{therapy} \\ 1 - S(\alpha, \beta, \text{Dose}(x,t)) & \text{for } t \in \text{therapy} \end{cases}$$

In this equation, the term $S(\alpha, \beta, \text{Dose}(x,t))$ represents the survival rate of cells exposed to a particular dose of radiation, where $\alpha$ and $\beta$ are parameters for a well-known radiation-exposure model.

As another example, the model can be expanded to take into account angiogenesis within a tumor. As summarized below, the expanded computational model that includes the angiogenic cascade, referred to as the "PIHNA model," is expressed as five linked partial differential equations describing the interactions between normoxic (c), hypoxic (h), necrotic (n) and endothelial cells (v) with angiogenic factors (a):

$$\frac{\partial c}{\partial t} = \underbrace{\nabla \cdot (D(1-T)\nabla c)}_{\substack{\text{Net dispersal of} \\ \text{normoxic} \\ \text{glioma cells}}} + \underbrace{\rho c(1-T)}_{\substack{\text{Net proliferation of} \\ \text{normoxic} \\ \text{glioma cells}}} +$$
$$\underbrace{\gamma hV}_{\substack{\text{Conversion of} \\ \text{hypoxic to} \\ \text{normoxic}}} - \underbrace{\beta c(1-V)}_{\substack{\text{Conversion} \\ \text{of normoxic to} \\ \text{hypoxic}}} - \underbrace{\alpha_n nc}_{\substack{\text{Conversion} \\ \text{of normoxic to} \\ \text{necrotic}}}$$

$$\frac{\partial h}{\partial t} = \underbrace{\nabla \cdot (D(1-T)\nabla h)}_{\substack{\text{Dispersal of} \\ \text{hypoxic} \\ \text{glioma cells}}} - \underbrace{\gamma hV}_{\substack{\text{Conversion of} \\ \text{hypoxic to} \\ \text{normoxic}}} + \underbrace{\beta c(1-V)}_{\substack{\text{Conversion} \\ \text{of normoxic to} \\ \text{hypoxic}}} - \underbrace{(\alpha_h h(1-V) + \alpha_n nh)}_{\substack{\text{Conversion} \\ \text{of hypoxice to} \\ \text{necrotic}}}$$

$$\frac{\partial n}{\partial t} = \underbrace{\alpha_h h(1-V) + \alpha_n n(c+h+v)}_{\text{Conversion of hypoxic, normoxic and vasculature to necrotic}}$$

$$\frac{\partial v}{\partial t} = \underbrace{\nabla \cdot (D_v(1-T)\nabla v)}_{\substack{\text{Dispersal of} \\ \text{vasculature}}} + \underbrace{\mu \frac{a}{K_m + a} v(1-T)}_{\substack{\text{Net proliferation} \\ \text{of vasculature}}} - \underbrace{\alpha_n nv}_{\substack{\text{Conversion of vasculature} \\ \text{to necrotic}}}$$

$$\frac{\partial a}{\partial t} = \underbrace{\nabla \cdot (D_a \nabla a)}_{\substack{\text{Diffusion of} \\ \text{angiogenic} \\ \text{factors}}} + \underbrace{\delta_c c + \delta_h h}_{\substack{\text{Net production} \\ \text{of angiogenic factors}}} -$$
$$\underbrace{q\mu \frac{a}{K_m + a} v(1-T)}_{\substack{\text{Net consumption of} \\ \text{angiogenic factors}}} - \omega av - \underbrace{\lambda a}_{\substack{\text{Decay of} \\ \text{angiogenic factors}}}$$

where $V = v/(c+h+v)$ and $T = (c+h+v+n)/K$.

The PIHNA-model definition begins with normoxic (c) glioma cells that are assumed to move randomly away from high tumor cell concentration (i.e., diffuse) in the tissue at a rate D and to proliferate at a rate $\rho$. These normoxic glioma cells compete for space with other neighboring cells. When the oxygen supply, determined by the relative amount of vasculature supplying the tissue, is insufficient, normoxic glioma cells convert to a hypoxic state h at a rate $\beta$. When oxygen continues to be inadequate, the hypoxic cells become necrotic at a rate $\alpha$. Both of these processes correlate positively with the metabolic demands of the tumor, so $\beta$ and $\alpha_h$ are proportional to $\rho$. On the other hand, when the oxygen supply increases at a later time and becomes sufficient, then hypoxic glioma cells will convert back to a normoxic state at a rate $\gamma$. It is possible for $\gamma$ to correlate negatively with $\rho$, again by reasoning of metabolism; however, $\gamma$ is assumed fixed, with $\alpha_h$ considered to adequately describe the greater tendency towards hypoxia caused by increased metabolic demands. Necrotic cells that come into contact with other cells can induce those viable cells to also become necrotic at a rate $\alpha_n$.

FIG. 10 illustrates an alternative method for estimating the parameters $\rho$ and D according to one embodiment of the present invention. As shown in FIG. 10, a matrix of tumor-growth models, with specific values of parameters $\rho$ and D, is constructed using the above-discussed PIHNA model. In FIG. 10, this matrix of models is represented as a two-dimensional plane 1002 indexed by a $\rho$-value axis 1004 and a D-value axis 1006. For each value of $$\frac{\rho}{D},$$

there is a line, such as line 1006, with slope $$\frac{\rho}{D}$$

extending from the origin 1010 outward. In the first-described two-image method, the velocity of the tumor-expansion wavefront is computed, and the velocity dependence on $\rho$ and D is used as a second equation in two unknowns to allow $\rho$ and D to be computed. However, the equivalent radius of the necrotic tissue within a tumor, T0, is obtained from T1 and/or T2 MRI images obtained at a single point in time, to provide a third observed value, or parameter. It turns out that the equivalent radius of the tumor, T0, is computed from the PIHNA models created for each discrete $\rho$ and D value, represented by the two-dimensional plane 1002 in FIG. 10. The models that predict particular T0 values form isocurves, such as isocurve 1012, in the $\rho$-and-D-parameterized model space. The ratio $$\frac{\rho}{D}$$

can be computed from a T1 and a T2 image as discussed above with reference to the first-described two-image method, by an analytical method. The equivalent radius of the necrotic portion of the tumor T0 can be computed from either the T1 or T2 image, or by one or more additional types of imaging techniques. In order to determine $\rho$ and D, the intersection between the line with slope $$\frac{\rho}{D},$$

such as line 1006 in FIG. 10, and the isocurve corresponding to the observed equivalent radius of the necrotic region of the tumor, such as isocurve 1014 in FIG. 10, is determined. In FIG. 10, an intersection between $$\frac{\rho}{D}$$

line 1006 and isocurve 1014 is shown as point 1016. The $\rho$ and D values can then be directly obtained from the intersection point as the $\rho$ and D coordinates of the intersection point, illustrated by dashed lines 1020 and 1022 and the intersection points 1024 and 1026 of the dashed lines and the coordinate axes in FIG. 10. Therefore, $\rho$ and D parameters that characterize a tumor is obtained, by the first-discussed method, from two different MRI images taken at two different times, or, using the above-described alternative method, from a single T1, T2 image and from a pre-computed $\rho$-and-D-parameterized space of PIHNA computational models or other computational models for tumor growth. In practice, rather than obtaining a single intersection point, a small region of intersection is obtained, reflecting imprecision in estimating T0 and $$\frac{\rho}{D},$$

providing generally small ranges of $\rho$ and D values.

Extensive analysis and characterization of glioblastomas in glioblastoma patients has revealed that the parameters $\rho$ and D, corresponding to proliferation and invasion parameters for tumor growth, do, indeed, characterize clinically observed glioblastoma growth in glioblastoma patients. The ratio $$\frac{\rho}{D}$$

can be interpreted as the relative steepness of the gradient of invading cells peripheral to the tumor surface as seen in a T1 image. Thus, the ratio $$\frac{\rho}{D}$$

is proportional to the proliferative nature of a tumor. Tumors with high $$\frac{\rho}{D}$$

ratios would be expected to show distinct borders and elevated necrosis associated with hypoxia due to crowding and other microenvironmental constraints inherent to highly proliferative tumors with relatively low invasion. The ratio $$\frac{D}{\rho},$$

often referred to as the "invisibility index," provides an estimate of the number or concentration of diffusely invading tumor cells peripheral to the imaged tumor boundary. Tumors with high $$\frac{D}{\rho}$$

values generally require applying more aggressive treatment to a containing volume significantly larger than the observed tumor volume. The determination of ρ and D parameter values, using biological imaging combined with computational modeling, thus provides useful and easy-to-interpret quantitative characteristics of tumor growth that can directly inform medical prognosis and treatment planning.

FIG. 11 provides a control-flow diagram for a routine "tumor-growth analysis" that represents one embodiment of the present invention. This method is carried out in an electronic computing system under software control. In step 1102, an initial medical image of the tumor is obtained at time $t_1$. In step 1104, a second image of the tumor is obtained at time $t_2$, using the same imaging technique. In step 1106, either a complementary image, using a different imaging technique, is obtained at time $t_2$ or a complementary image pair is obtained at time $t_3$. In step 1108, a first numerical value is calculated for the wave-front velocity v, as discussed above, using the initial and second images. In step 1110, a second numerical value for the ratio $$\frac{\rho}{D}$$

is computed using an analytical function and a lookup table, as discussed above. In step 1112, D and ρ are computed from the first and second numerical values, as discussed above. In addition, a scalar or tensor field D(r) for a spatially varying diffusion coefficient can be determined, using various methods discussed above. A numerical DM/BECP-model is then obtained, in step 1114. In step 1116, the parameters D, ρ, and, optionally, D(r) may be stored in an electronic database for the patient, so that the DM/BECP-model can be subsequently regenerated. In step 1118, the routine "use model" is called to provide various derived characteristics for the tumor.

FIG. 12 provides a control-flow diagram for a routine "use model" that represents one embodiment of the present invention. In step 1202, the routine "use model" determines whether a particular DM/BECP model is currently in memory, and, when not, uses a patient identifier to retrieve the DM/BECP model from an electronic database. The entire DM/BECP model may be retrieved or, alternatively, the DM/BECP model may be regenerated from retrieved parameter values. Then, in the for-loop of steps 1207-1214, requests for results derived from the DM/BECP model or for parameter values of the DM/BECP model are received from a user, and the requested derived results and parameter values output to a user or to an electronic data-processing or data-storage device on behalf of a user. Derived results may include a representation of the spatial extent of the tumor, in three dimensions, based on a threshold malignant-cell concentration, the $$\frac{\rho}{D}$$

ratio, indicative of tumor aggressiveness, and any of many other derived results. These results may be then used, by medical personnel, for disease prognosis, for therapy planning, for data-collection purposes to further medical research, and for a variety of additional purposes.

FIG. 13 provides a control-flow diagram for the alternative, single-image method for determining ρ and D parameters for a tumor. In step 1302, T1 and T2 MRI images are obtained from a patient at a single point in time. In step 1304, the ratio $$\frac{\rho}{D}$$

is computed by the analytical method discussed above with reference to the two-image method. In step 1306, the equivalent radius of the necrotic region of the tumor, T0, is computed from the T1, T2 MRI image. In step 1308, the intersection point between a line with slope $$\frac{\rho}{D}$$

and the isocurve for the computed T0 value is found in ρ-and-D-parameterized model space, allowing ρ and D to be obtained, in step 1310, as the ρ-and-D coordinates of the intersection point between the line and isocurve.

Although the present invention has been described in terms of particular embodiments, it is not intended that the invention be limited to these embodiments. Modifications will be apparent to those skilled in the art. For example, models other than the DM/BECP model may be employed to model various types of tumors, the models containing parameters different from, or in addition to, D and ρ. Imaging techniques, other than T1 imaging and T2 imaging, may be used to determine tumor volumes and regions of hypointensity, of T0 regions, used for computing D and ρ. Additional types of imaging, using labeled DNA monomer analogues, labeled metabolites, and other substances, can be used to obtain additional characterization of tumor volumes, necrotic volumes within tumors, and additional parameters and characteristics of tumors that can be incorporated into additionally expanded computational models. In the above discussion, a first, two-time-point based method for obtaining D and ρ was discussed. This method is easily extended to makes use of additional data generated at additional time points, and can thus be considered to be an n-time-point method. Additional data can provide more accurate estimation of D and ρ in the general, n-time-point method. A variety of implementations of the present invention may be obtained by varying development parameters, including programming language, operating system platform, control structures, data structures, modular organization, and other such parameters. Method embodiments of the present invention may be incorporated into imaging and/or image-analysis equipment, as well as in various hospital information systems.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby It is intended that the scope of the invention be defined by the following claims and their equivalents:

1. A computer-implemented method of modeling tumor growth for guiding medical intervention, comprising:
   (a) calculating ρ/D, an observed ratio of a malignant cell proliferation coefficient, ρ, to a diffusion coefficient, D, from one or more different measures of tumor volume from either a single or multiple images of a tumor, which calculating comprises mapping the following formula derived from an analytic solution of a linear tumor model to a non-linear tumor model:

$$\left(\frac{\rho}{D}\right)_c = \left[\frac{4\ln\left(\frac{t_1}{t_2}\right)}{(T2r_{eqv})^2 - (T1r_{eqv})^2}\right]\left[\left[\frac{T1r_{eqv}^2 \ln\left(\frac{t_1}{t_2}\right)}{(T2r_{eqv})^2 - (T1r_{eqv})^2}\right] + \ln\frac{t_1 k}{N_0}\left[\frac{\prod(T2r_{eqv}^2 - T1r_{eqv}^2)}{\ln\left(\frac{t_1}{t_2}\right)}\right]^{3/2}\right]$$

where
$T1r_{eqv}$ and $T2r_{eqv}$ are the radii of the equivalent, spherical tumor volumes corresponding to the one or more different measures of tumor volume, respectively;
$t_1$ and $t_2$ are threshold tumor cell concentrations for two of said measures of tumor volume,
k is maximum malignant-cell concentration; and
$N_0$ is an initial malignant-cell concentration or number;
   (b) obtaining a value for D and a value for ρ; and
   (c) generating a computational model for growth of the tumor in a cancer patient using the values of D and ρ obtained in step (b);
wherein steps (a)-(c) are performed using a computer system.

2. The method of claim 1, further comprising calculating a tensor diffusion coefficient, D(r), prior to step (c), to generate the computational model to generate the computational model.

3. The method of claim 2, further comprising storing the computational model, D, ρ, D(r) or a combination thereof in an electronic database.

4. The method of claim 1, wherein the measures of tumor volume are from two different types of medical imaging performed at approximately the same time.

5. The method of claim 1, wherein, given a size of the tumor necrotic region (T0) measured from an image, the values of D and ρ are obtained by finding an intersection point between:
   (i) a line with slope ρ/D; and
   (ii) an isocurve corresponding to the observed equivalent radius of T0 provided by a non-linear proliferation invasion hypoxia necrosis angiogenesis (PIHNA) model isocurve.

6. The method of claim 1, wherein a first and a second image are obtained
   (i) at two separate times by the same imaging technique; or
   (ii) at approximately the same time using different imaging techniques.

7. The method of claim 1, wherein aggressiveness and/or prognosis of the tumor is determined by ρ/D.

8. The method of claim 1, wherein the computational model comprises one or more additional terms to predict the effects of cancer therapy, to model angiogenesis within the tumor, or both.

9. The method of claim 1, wherein the tumor is a glioma.

10. The method of claim 1, further comprising calculating a concentration wave-front velocity of tumor expansion using one or more of said images.

11. The method of claim 10, wherein ρ/D is calculated from an image or images obtained at two separate times, $time_0$ and $time_1$, using the same imaging technique.

12. The method of claim 11, wherein the concentration wavefront velocity of tumor expansion is calculated as
   (i) equivalent radii of a spherical tumor of volume equal to the volumes of the tumor at times $time_0$ and $time_1$ using a threshold tumor cell concentration; or as
   (ii) an average linear rate of expansion of the tumor along directions normal to a the tumor's surface.

13. The method of claim 10, wherein the observed ratio ρ/D is obtained from a lookup table.

14. The method of claim 13, wherein the values for D and ρ are obtained using the concentration wave-front velocity and observed ratio of ρ/D.

15. A computer program product for modeling tumor growth and for guiding medical intervention comprising a non-transitory computer readable medium which, when executed by a computer causes a method to be performed, the method comprising:
   (a) calculating a ratio, ρ/D, an observed ratio of a malignant cell proliferation coefficient, ρ, to a diffusion coefficient, D, from one or more different measures of tumor volume from either a single or multiple images of a tumor, which calculating comprises mapping the following formula derived from an analytic solution of a linear tumor model to a non-linear tumor model:

$$\left(\frac{\rho}{D}\right)_c = \left[\frac{4\ln\left(\frac{t_1}{t_2}\right)}{(T2r_{eqv})^2 - (T1r_{eqv})^2}\right]\left[\left[\frac{T1r_{eqv}^2 \ln\left(\frac{t_1}{t_2}\right)}{(T2r_{eqv})^2 - (T1r_{eqv})^2}\right] + \ln\frac{t_1 k}{N_0}\left[\frac{\prod(T2r_{eqv}^2 - T1r_{eqv}^2)}{\ln\left(\frac{t_1}{t_2}\right)}\right]^{3/2}\right]$$

where
$T1r_{eqv}$ and $T2r_{eqv}$ are the radii of the equivalent, spherical tumor volumes corresponding to the one or more different measures of tumor volume, respectively;
$t_1$ and $t_2$ are threshold tumor cell concentrations for two of said measures of tumor volume,
k is maximum malignant-cell concentration; and
$N_0$ is an initial malignant-cell concentration or number;
   (b) obtaining a value for D and a value for ρ; and
   (c) generating a computational model for tumor growth of the tumor in a cancer patient using the values of D and ρ obtained in (b);
wherein the computer-readable medium is non-transitory.

16. The computer program product of claim 15, wherein the method further comprises calculating a tensor diffusion coefficient, D(r), prior to step (c) to generate the computational model.

17. The computer program product of claim 16, wherein the method further comprises storing the computational model, D, ρ, D(r) or a combination thereof in an electronic database.

18. The computer program product of claim 16, wherein the measures of tumor volume are performed by two different types of medical imaging taken at approximately the same time.

19. The computer program product of claim 15, wherein, given a size of the tumor necrotic region (T0) measured from an image, the values of the D and ρ are obtained by finding an intersection point between:
   (i) a line with slope ρ/D; and
   (ii) an isocurve corresponding to the observed equivalent radius of T0, provided by a non-linear PIHNA model.

20. The computer program product of claim 15, wherein the aggressiveness and/or prognosis of the tumor is determined by ρ/D.

21. The computer program product of claim 15, wherein the tumor is a glioma.

22. The computer program product of claim 15, wherein the computational model comprises one or more additional terms to predict the effects of cancer therapy, to model angiogenesis within the tumor, or both.

23. The computer program product of claim 15, wherein the computer program product is incorporated into imaging equipment, image analysis equipment, or both.

24. The computer program product of claim 15, wherein the computer program product is incorporated into a hospital information system.

25. The computer program product of claim 15, wherein the method further comprises calculating a concentration wave-front velocity of tumor expansion from one or more of said images.

26. The computer program product of claim 25, wherein ρ/D is calculated from an image or images obtained at two separate times, $time_0$ and $time_1$, using the same imaging technique.

27. The computer program product of claim 26, wherein the concentration wave-front velocity of tumor expansion is calculated as
   (i) equivalent radii of a spherical tumor of volume equal to the volumes of the tumor at times $time_0$ and $time_1$ using a threshold tumor cell concentration; or as
   (ii) an average linear rate of expansion of the tumor along directions normal to the tumor's surface.

28. The computer program product of claim 25, wherein the observed ratio ρ/D is obtained from a lookup table.

29. The computer program product of claim 28, wherein a first and a second image are obtained
   (i) at two separate times by the same imaging technique; or
   (ii) at approximately the same time using different imaging techniques.

30. The computer program product of claim 28, wherein the values for D and ρ are obtained using the concentration wave-front velocity and observed ratio of ρ/D.

31. A system for modeling tumor-growth in a patient, comprising:
   (a) one or more electronic computational processors;
   (b) one or more electronic memories;
   (c) the computer program product of claim 15;
   (d) a set of computer instructions stored in the one or more electronic memories configured to execute on the one or more electronic computational processors and generate a computational model that estimates tumor-cell concentrations at one or more positions within a tumor-containing tissue; and
   (e) an output device for presenting results generated by the computational model to a user as a representation or prediction of the spatial extent of the tumor, the aggressiveness of the tumor, or both.

32. The system of claim 31 wherein the computational model comprises:
   (i) a cell-proliferation component that includes a patient-specific tumor-cell migration coefficient representing a spatial rate of change of a tumor-cell concentration gradient at a position within the tumor-containing tissue; and
   (ii) a diffusive-migration component that includes a patient-specific tumor-cell proliferation coefficient that represents an exponential tumor-cell proliferation rate.

33. The system of claim 32, that further comprises:
   (iii) a set of computer instructions stored in the one or more electronic memories configured to execute on the one or more electronic computational processors and estimate the patient-specific tumor-cell proliferation coefficient and the patient-specific tumor-cell migration coefficient for a specific tumor within a specific tissue of a patient.

34. The system of claim 33, wherein estimation of the patient-specific tumor-cell proliferation coefficient and the patient-specific tumor-cell migration coefficient is accomplished by calculating a first value for ρ/D for the tumor using a first stored computational relationship between:
   (i) the ratio ρ/D; and
   (ii) two equivalent radii $r_1$ and $r_2$ of the tumor, calculated from
      (A) at least two images, acquired by (1) the same or different methods, and (2) at approximately the same time,
      (B) threshold tumor-cell concentrations for the two images, and
      (C) constants related to initial and maximum tumor cell concentrations.

35. The system of claim 34 wherein the calculation of a first numerical value for ρ/D is accomplished by:
   (a) calculating an initial ratio of ρ/D from the first stored computational relationship; and
   (b) applying to the calculated initial ρ/D a correction obtained from a lookup table.

36. The system of claim 34, wherein the method further comprises the steps of:
   (a) determining a wave front velocity of tumor expansion from at least two images acquired by the same method at least two different times, $time_0$ and $time_1$; and
   (b) computing a second numerical value which is a product of the specific tumor cell migration coefficient and the specific tumor cell proliferation coefficient using a second stored computational relationship relating the tumor cell migration coefficient to velocity of tumor expansion; and
   (c) determining a third numerical value which is the specific tumor cell proliferation coefficient from the calculated first and second numerical values; and
   (d) determining a fourth numerical value which is the specific tumor cell migration coefficient from the computed first and second numerical values.

37. The system of claim 34, wherein the method further comprises:
   (a) determining an equivalent radius $r_n$ of necrotic tissue within the tumor from the at least two images;
   (b) determining an intersection, on a two-dimensional matrix of pre-computed computational models, between (1) a line of slope equal to (i) the ratio of the specific tumor-cell proliferation coefficient to the specific tumor-cell migration coefficient and
(2) an isocurve with a constant-equivalent-radius-of-necrotic-tissue value, produced by computational models of the two-dimensional matrix, equal to the determined equivalent radius $r_n$; and
(c) calculating a plurality of numerical values for the specific tumor-cell proliferation coefficient and the specific tumor-cell migration coefficient from indices of the computed intersection;

wherein the two-dimensional matrix of pre-computed computational models comprises a plurality of tumor-cell proliferation coefficients and tumor-cell migration coefficients, each pre-computed computational model indexed by a pair of numeric values representing the tumor cell proliferation coefficients and the tumor cell migration coefficients.

* * * * *